United States Patent
Bolene et al.

(10) Patent No.: US 11,836,670 B2
(45) Date of Patent: *Dec. 5, 2023

(54) SHIPPING EVENTS AND RECEIVING EVENTS

(71) Applicant: GLOBAL HEALTHCARE EXCHANGE, LLC, Louisville, CO (US)

(72) Inventors: David Bolene, Austin, TX (US); Eric Bolinger, Broomfield, CO (US); Margot Drees, Boulder, CO (US); Janine Fornarola, Arvada, CO (US)

(73) Assignee: GLOBAL HEALTHCARE EXCHANGE LLC, Louisville, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/160,884

(22) Filed: Jan. 27, 2023

(65) Prior Publication Data

US 2023/0177450 A1 Jun. 8, 2023

Related U.S. Application Data

(63) Continuation of application No. 16/785,097, filed on Feb. 7, 2020, now Pat. No. 11,593,748, which is a
(Continued)

(51) Int. Cl.
*G06Q 10/00* (2023.01)
*G06Q 10/0833* (2023.01)
(Continued)

(52) U.S. Cl.
CPC ....... *G06Q 10/0833* (2013.01); *G06K 7/1413* (2013.01); *G06Q 10/0832* (2013.01);
(Continued)

(58) Field of Classification Search
CPC ....... G06Q 10/08–0875; G06Q 10/06315–067
See application file for complete search history.

(56) References Cited

U.S. PATENT DOCUMENTS 6,249,774 B1 6/2001 Roden et al.
6,430,467 B1 8/2002 D'Amelio et al.
(Continued)

OTHER PUBLICATIONS

New EPC Standard For Information Services May Breathe Life Back Into RFID Market SupplyChainBrain, Jean V. Murphy, May 1, 2007 (Year: 2007).*
(Continued)

*Primary Examiner* — Hafiz A Kassim
*Assistant Examiner* — Scott M Ross
(74) *Attorney, Agent, or Firm* — SNELL & WILMER L.L.P.

(57) ABSTRACT

Systems and methods are directed to supply chain management. In particular, the tracking, tracing, authenticating, and reporting of supply chain events for products, is disclosed. Various embodiments can store, analyze, and track supply chain events and help to coordinate and maintain trading partner connections. Various embodiments also help to enhance patient safety, secure the supply chains for pharmaceuticals, medical devices, and other healthcare products, and help users to follow regulatory requirements.

19 Claims, 21 Drawing Sheets

Related U.S. Application Data continuation of application No. 16/778,348, filed on Jan. 31, 2020, now Pat. No. 11,042,830, which is a continuation of application No. 15/461,294, filed on Mar. 16, 2017, now Pat. No. 10,592,848, which is a continuation of application No. 13/804,955, filed on Mar. 14, 2013, now Pat. No. 9,633,325, which is a continuation of application No. 13/804,572, filed on Mar. 14, 2013, now Pat. No. 9,589,247.

(60) Provisional application No. 61/725,350, filed on Nov. 12, 2012.

(51) Int. Cl.
*G16H 40/20* (2018.01)
*G06Q 10/0832* (2023.01)
*G06K 7/14* (2006.01)
*G06Q 10/0631* (2023.01)
*G06Q 10/0637* (2023.01)

(52) U.S. Cl.
CPC ......... *G16H 40/20* (2018.01); *G06Q 10/0637* (2013.01); *G06Q 10/06315* (2013.01)

(56) References Cited

U.S. PATENT DOCUMENTS

| | | |
|---|---|---|
| 6,671,578 B1 | 12/2003 | D'Amelio et al. |
| 6,671,698 B2 | 12/2003 | Pickett et al. |
| 6,691,135 B2 | 2/2004 | Pickett et al. |
| 6,901,304 B2 | 5/2005 | Swan |
| 6,945,459 B2 | 9/2005 | Flanagan |
| 6,963,881 B2 | 11/2005 | Pickett et al. |
| 6,967,577 B2 | 11/2005 | Taylor et al. |
| 6,972,682 B2 | 12/2005 | Lareau et al. |
| 7,070,110 B2 | 7/2006 | Lapstun et al. |
| 7,091,861 B2 | 8/2006 | Schmidtberg et al. |
| 7,097,106 B2 | 8/2006 | Silverbrook et al. |
| 7,128,265 B2 | 10/2006 | Silverbrook et al. |
| 7,128,270 B2 | 10/2006 | Silverbrook et al. |
| 7,131,596 B2 | 11/2006 | Lapstun et al. |
| 7,136,832 B2 | 11/2006 | Li |
| 7,137,566 B2 | 11/2006 | Silverbrook et al. |
| 7,149,658 B2 | 12/2006 | Kadaba |
| 7,150,398 B2 | 12/2006 | Silverbrook et al. |
| 7,156,289 B2 | 1/2007 | Silverbrook et al. |
| 7,156,305 B2 | 1/2007 | Swan et al. |
| 7,159,777 B2 | 1/2007 | Silverbrook et al. |
| 7,175,089 B2 | 2/2007 | Silverbrook et al. |
| 7,178,718 B2 | 2/2007 | Silverbrook et al. |
| 7,178,719 B2 | 2/2007 | Silverbrook et al. |
| 7,178,769 B2 | 2/2007 | Magnusson et al. |
| 7,197,374 B2 | 3/2007 | Silverbrook et al. |
| 7,205,897 B2 | 4/2007 | Lin |
| 7,207,481 B2 | 4/2007 | Barenburg et al. |
| 7,207,483 B2 | 4/2007 | Silverbrook et al. |
| 7,207,485 B2 | 4/2007 | Silverbrook et al. |
| 7,225,979 B2 | 6/2007 | Silverbrook et al. |
| 7,243,849 B2 | 7/2007 | Lapstun et al. |
| 7,261,235 B2 | 8/2007 | Barenburg et al. |
| 7,267,273 B2 | 9/2007 | Silverbrook et al. |
| 7,267,275 B2 | 9/2007 | Cox |
| 7,270,266 B2 | 9/2007 | Silverbrook et al. |
| 7,278,571 B2 | 10/2007 | Schimdtberg et al. |
| 7,289,931 B2 | 10/2007 | Ebert |
| 7,296,737 B2 | 11/2007 | Silverbrook et al. |
| 7,314,177 B2 | 1/2008 | Lapstun |
| 7,314,181 B2 | 1/2008 | Lapstun |
| 7,319,397 B2 | 1/2008 | Chung |
| 7,333,015 B2 | 2/2008 | Ekstrom |
| 7,342,497 B2 | 3/2008 | Chung |
| 7,343,303 B2 | 3/2008 | Meyer et al. |
| 7,357,323 B2 | 4/2008 | Silverbrook et al. |
| 7,378,969 B2 | 5/2008 | Chan et al. |
| 7,380,712 B2 | 6/2008 | Silverbrook et al. |
| 7,383,284 B2 | 6/2008 | Heinrichs et al. |
| 7,383,984 B2 | 6/2008 | Silverbrook et al. |
| 7,383,991 B2 | 6/2008 | Silverbrook et al. |
| 7,385,509 B2 | 6/2008 | Taylor et al. |
| 7,389,921 B2 | 6/2008 | Lin et al. |
| 7,394,377 B2 | 7/2008 | Banerjee |
| 7,394,381 B2 | 7/2008 | Hanson et al. |
| 7,395,963 B2 | 7/2008 | Silverbrook et al. |
| 7,401,054 B1 | 7/2008 | Shah et al. |
| 7,417,543 B2 | 8/2008 | Bergman et al. |
| 7,423,535 B2 | 9/2008 | Chung et al. |
| 7,450,273 B2 | 11/2008 | Silverbrook et al. |
| 7,454,315 B2 | 11/2008 | Kadaba |
| 7,457,007 B2 | 11/2008 | Silverbrook et al. |
| 7,457,720 B2 | 11/2008 | Ebert |
| 7,464,879 B2 | 12/2008 | Silverbrook et al. |
| 7,465,929 B2 | 12/2008 | Vija |
| 7,467,093 B1 | 12/2008 | Newton et al. |
| 7,469,836 B2 | 12/2008 | Silverbrook et al. |
| 7,471,202 B2 | 12/2008 | Anderson |
| 7,479,877 B2 | 1/2009 | Mortenson et al. |
| 7,481,368 B2 | 1/2009 | Wang et al. |
| 7,482,931 B2 | 1/2009 | Lin |
| 7,484,662 B2 | 2/2009 | Schmidtberg et al. |
| 7,495,568 B2 | 2/2009 | Banerjee |
| 7,501,949 B2 | 3/2009 | Shah et al. |
| 7,504,954 B2 | 3/2009 | Spaeder |
| 7,506,808 B2 | 3/2009 | Silverbrook et al. |
| 7,518,502 B2 | 4/2009 | Austin |
| 7,522,043 B2 | 4/2009 | English et al. |
| 7,525,431 B2 | 4/2009 | Britton et al. |
| 7,537,157 B2 | 5/2009 | Silverbrook et al. |
| 7,537,160 B2 | 5/2009 | Silverbrook et al. |
| 7,545,267 B2 | 6/2009 | Stortoni |
| 7,564,352 B2 | 7/2009 | Ekstrom |
| 7,564,364 B2 | 7/2009 | Zweig |
| 7,566,009 B2 | 7/2009 | Lapstun et al. |
| 7,568,629 B2 | 8/2009 | Lapstun et al. |
| 7,574,308 B1 | 8/2009 | Esbeck |
| 7,590,548 B2 | 9/2009 | Meyer et al. |
| 7,602,288 B2 | 10/2009 | Broussard |
| 7,605,940 B2 | 10/2009 | Silverbrook et al. |
| 7,612,673 B2 | 11/2009 | Onderko et al. |
| 7,612,923 B2 | 11/2009 | Rusman et al. |
| 7,615,003 B2 | 11/2009 | Stefanchik et al. |
| 7,617,976 B2 | 11/2009 | Silverbrook et al. |
| 7,621,447 B1 | 11/2009 | Sarma et al. |
| 7,637,419 B2 | 12/2009 | Silverbrook et al. |
| 7,637,437 B2 | 12/2009 | Lapstun et al. |
| 7,639,140 B2 | 12/2009 | Shah |
| 7,648,068 B2 | 1/2010 | Silverbrook et al. |
| 7,654,454 B2 | 2/2010 | Silverbrook et al. |
| 7,657,073 B2 | 2/2010 | Sun et al. |
| 7,660,890 B2 | 2/2010 | Banerjee |
| 7,667,604 B2 | 2/2010 | Ebert et al. |
| 7,676,299 B2 | 3/2010 | Clarke et al. |
| 7,676,382 B2 | 3/2010 | Silverbrook et al. |
| 7,685,026 B1 | 3/2010 | McGrady et al. |
| 7,693,727 B2 | 4/2010 | Moore |
| 7,702,187 B2 | 4/2010 | Rusman et al. |
| 7,702,522 B1 | 4/2010 | Sholem |
| 7,706,860 B2 | 4/2010 | McGee |
| 7,721,961 B2 | 5/2010 | Silverbrook et al. |
| 7,729,743 B2 | 6/2010 | Sabczynski et al. |
| 7,729,927 B2 | 6/2010 | Cunningham |
| 7,737,857 B2 | 6/2010 | Ebert et al. |
| 7,740,167 B2 | 6/2010 | Silverbrook et al. |
| 7,742,804 B2 | 6/2010 | Faul |
| 7,747,477 B1 | 6/2010 | Louie et al. |
| 7,748,624 B2 | 7/2010 | Silverbrook et al. |
| 7,751,932 B1 | 7/2010 | Fedor et al. |
| 7,753,257 B2 | 7/2010 | Silverbrook et al. |
| 7,756,902 B2 | 7/2010 | Lin |
| 7,761,334 B2 | 7/2010 | Pickett et al. |
| 7,761,348 B2 | 7/2010 | Amling et al. |
| 7,783,500 B2 | 8/2010 | Meyer et al. |
| 7,801,742 B2 | 9/2010 | Silverbrook et al. |
| 7,805,499 B2 | 9/2010 | Banerjee |

(56) References Cited

U.S. PATENT DOCUMENTS

| | | |
|---|---|---|
| 7,810,726 B2 | 10/2010 | De La Huerga |
| 7,817,045 B2 | 10/2010 | Onderko |
| 7,819,323 B2 | 10/2010 | Silverbrook et al. |
| 7,826,889 B2 | 11/2010 | David et al. |
| 7,835,785 B2 | 11/2010 | Scully et al. |
| 7,835,823 B2 | 11/2010 | Sillman et al. |
| 7,835,954 B2 | 11/2010 | Banerjee |
| 7,839,289 B2 | 11/2010 | Chung et al. |
| 7,853,480 B2 | 12/2010 | Taylor et al. |
| 7,853,536 B2 | 12/2010 | Amling et al. |
| 7,866,543 B2 | 1/2011 | Asher et al. |
| 7,868,754 B2 | 1/2011 | Salvat |
| 7,874,481 B2 | 1/2011 | Silverbrook et al. |
| 7,878,408 B2 | 2/2011 | Lapstun et al. |
| 7,878,416 B2 | 2/2011 | Lapstun et al. |
| 7,890,342 B1 | 2/2011 | Yruko |
| 7,895,092 B2 | 2/2011 | Amling et al. |
| 7,900,819 B2 | 3/2011 | Silverbrook et al. |
| 7,900,833 B2 | 3/2011 | Silverbrook et al. |
| 7,900,841 B2 | 3/2011 | Lapstun et al. |
| 7,904,470 B2 | 3/2011 | Kuerschner et al. |
| 7,904,548 B2 | 3/2011 | Shah et al. |
| 7,905,401 B2 | 3/2011 | Silverbrook et al. |
| 7,909,249 B2 | 3/2011 | Bagozzi et al. |
| 7,918,399 B2 | 4/2011 | Silverbrook et al. |
| 7,930,142 B2 | 4/2011 | Kadaba |
| 7,932,828 B2 | 4/2011 | Britton et al. |
| 7,934,650 B2 | 5/2011 | Silverbrook et al. |
| 7,936,270 B2 | 5/2011 | Britton et al. |
| 7,937,244 B2 | 5/2011 | Kadaba |
| 7,937,297 B2 | 5/2011 | Boland et al. |
| 7,937,298 B2 | 5/2011 | Shah |
| 7,946,485 B2 | 5/2011 | Silverbrook et al. |
| 7,946,487 B2 | 5/2011 | Silverbrook et al. |
| 7,959,079 B2 | 6/2011 | Silverbrook et al. |
| 7,961,360 B2 | 6/2011 | Rusman et al. |
| 7,961,921 B2 | 6/2011 | Mahesh |
| 7,962,349 B2 | 6/2011 | Silverbrook et al. |
| 7,969,306 B2 | 6/2011 | Ebert |
| 7,970,174 B2 | 6/2011 | Goldbach |
| 7,974,925 B2 | 7/2011 | Shah et al. |
| 7,979,355 B2 | 7/2011 | Shah et al. |
| 7,980,467 B2 | 7/2011 | Silverbrook et al. |
| 7,993,353 B2 | 8/2011 | Roβner et al. |
| 7,995,827 B2 | 8/2011 | Wagner et al. |
| 8,002,174 B2 | 8/2011 | Coyne et al. |
| 8,022,943 B2 | 9/2011 | Silverbrook et al. |
| 8,028,907 B2 | 10/2011 | Silverbrook et al. |
| 8,034,294 B1 | 10/2011 | Goldberg |
| 8,042,738 B2 | 10/2011 | Cloix |
| 8,044,778 B2 | 10/2011 | Monroe |
| 8,046,243 B2 | 10/2011 | Winkler |
| 8,079,517 B2 | 12/2011 | Silverbrook et al. |
| 8,111,159 B2 | 2/2012 | Andreasson et al. |
| 8,111,431 B2 | 2/2012 | Silverbrook et al. |
| 8,112,175 B2 | 2/2012 | Handfield et al. |
| 8,113,424 B2 | 2/2012 | Philippe |
| 8,285,561 B2 | 2/2012 | Andreasson et al. |
| 8,132,729 B2 | 3/2012 | Silverbrook et al. |
| 8,136,720 B2 | 3/2012 | Silverbrook et al. |
| 8,136,728 B2 | 3/2012 | Turner et al. |
| 8,140,402 B1 | 3/2012 | Mesaros |
| 8,149,111 B2 | 4/2012 | Monroe |
| 8,152,072 B2 | 4/2012 | Silverbrook et al. |
| 8,154,421 B2 | 4/2012 | Saltzman et al. |
| 8,159,349 B2 | 4/2012 | McAllister et al. |
| 8,162,837 B2 | 4/2012 | Moehring et al. |
| 8,165,901 B2 | 4/2012 | Raymond |
| 8,165,929 B2 | 4/2012 | Chudy et al. |
| 8,170,900 B2 | 5/2012 | Young et al. |
| 8,174,383 B1 | 5/2012 | Chung et al. |
| 8,176,062 B2 | 5/2012 | Fife et al. |
| 8,196,825 B2 | 6/2012 | Turner et al. |
| 8,212,658 B2 | 7/2012 | Monroe |
| 8,212,674 B2 | 7/2012 | Howarth et al. |
| 8,224,423 B2 | 7/2012 | Faul |
| 8,226,610 B2 | 7/2012 | Edwards et al. |
| 8,228,198 B2 | 7/2012 | McAllister |
| 8,239,005 B2 | 8/2012 | Wright et al. |
| 8,242,907 B2 | 8/2012 | Butler et al. |
| 8,242,908 B2 | 8/2012 | Butler et al. |
| 8,242,911 B2 | 8/2012 | Moore et al. |
| 8,244,747 B2 | 8/2012 | Agrawal et al. |
| 8,248,238 B2 | 8/2012 | Butler et al. |
| 8,248,239 B2 | 8/2012 | Butler et al. |
| 8,249,886 B2 | 8/2012 | Meyer et al. |
| 8,253,567 B2 | 8/2012 | Butler et al. |
| 8,269,630 B2 | 9/2012 | Butler et al. |
| 8,271,308 B2 | 9/2012 | Winkler |
| 8,275,181 B2 | 9/2012 | Muradyan et al. |
| 8,279,065 B2 | 10/2012 | Butler et al. |
| 8,279,067 B2 | 10/2012 | Berger et al. |
| 8,280,686 B2 | 10/2012 | Kadaba |
| 8,281,994 B1 | 10/2012 | Wass et al. |
| 8,284,055 B2 | 10/2012 | Butler et al. |
| 8,284,461 B2 | 10/2012 | Rusman et al. |
| 8,285,517 B2 | 10/2012 | Sillman et al. |
| 8,285,598 B2 | 10/2012 | Mesaros |
| 8,285,607 B2 | 10/2012 | Danilewitz |
| 8,286,222 B2 | 10/2012 | Silverbrook et al. |
| 8,287,816 B2 | 10/2012 | Kral |
| 8,292,174 B2 | 10/2012 | Bagozzi et al. |
| 8,294,579 B2 | 10/2012 | Butler et al. |
| 8,295,909 B2 | 10/2012 | Goldbach |
| 8,348,160 B2 | 1/2013 | Asher et al. |
| 9,112,895 B1 | 8/2015 | Lin |
| 9,328,537 B2 | 5/2016 | Joseph |
| 2002/0010661 A1 | 1/2002 | Waddington |
| 2002/0095322 A1 | 7/2002 | Zarefoss |
| 2002/0111819 A1 | 8/2002 | Li |
| 2003/0227392 A1 | 12/2003 | Ebert |
| 2006/0106718 A1 | 5/2006 | Spellman |
| 2006/0142895 A1 | 6/2006 | Waddington |
| 2008/0109411 A1 | 5/2008 | Young et al. |
| 2008/0114744 A1 | 5/2008 | Colby |
| 2009/0091451 A1 | 4/2009 | Jones et al. |
| 2009/0271372 A1 | 10/2009 | Fife et al. |
| 2009/0307032 A1 | 12/2009 | Tribe et al. |
| 2010/0153870 A1 | 6/2010 | Hoffmann |
| 2010/0299763 A1 | 11/2010 | Marcus et al. |
| 2010/0329464 A1 | 12/2010 | Kerschbaum |
| 2011/0071871 A1 | 3/2011 | Wong et al. |
| 2011/0137800 A1 | 6/2011 | Kerschbaum et al. |
| 2013/0276134 A1 | 10/2013 | Meredith et al. |
| 2014/0046479 A1 | 2/2014 | Marrese et al. |
| 2014/0075567 A1 | 3/2014 | Raleigh et al. |
| 2014/0136218 A1 | 5/2014 | Bolen et al. |
| 2015/0022359 A1 | 1/2015 | Joseph |
| 2020/0167725 A1 | 5/2020 | Bolene et al. |

OTHER PUBLICATIONS

USPTO, Notice of Allowance dated Mar. 20, 2023 in U.S. Appl. No. 17/320,615.
EPC Information Services (EPCIS) Version 1.0.1 Specification. Errata Approved by TSC on Sep. 21, 2007 (Year: 2007).
Healthcare, "Implementation Guideline: Applying GS1 Standards for DSCSA and Traceability", Release 1.2, Nov. 7, 2016 (Year:2016).
International Searching Authority, International Search Report and Written Opinion dated Feb. 27, 2014 in Application No. PCT/US2013/069392.
International Preliminary Examing Authority, International Preliminary Report on Patentability dated Feb. 16, 2015 in Application No. PCT/US2013/069392.
USPTO, Office Action dated Apr. 13, 2015 in U.S. Appl. No. 13/904,572.
USPTO, Final Office Action dated Jun. 26, 2015 in U.S. Appl. No. 13/904,572.
USPTO, Advisory Action dated Aug. 27, 2015 in U.S. Appl. No. 13/904,572.
USPTO, Office Action dated Oct. 2, 2015 in U.S. Appl. No. 13/904,572.

(56) References Cited

OTHER PUBLICATIONS

USPTO, Final Office Action dated Mar. 11, 2016 in U.S. Appl. No. 13/904,572.
USPTO, Advisory Action dated Jun. 3, 2016 in U.S. Appl. No. 13/904,572.
USPTO, Office Action dated Jul. 1, 2016 in U.S. Appl. No. 13/904,572.
USPTO, Final Office Action dated Nov. 3, 2016 in U.S. Appl. No. 13/904,572.
USPTO, Notice of Allowance dated Jan. 19, 2017 in U.S. Appl. No. 13/904,572.
USPTO, Office Action dated Apr. 9, 2015 in U.S. Appl. No. 13/804,955.
USPTO, Final Office Action dated Jun. 29, 2015 in U.S. Appl. No. 13/804,955.
USPTO, Advisory Action dated Aug. 20, 2015 in U.S. Appl. No. 13/804,955.
USPTO, Office Action dated Oct. 2, 2015 in U.S. Appl. No. 13/804,955.
USPTO, Final Office Action dated Mar. 11, 2016 in U.S. Appl. No. 13/804,955.
USPTO, Advisory Action dated Jun. 3, 2016 in U.S. Appl. No. 13/804,955.
USPTO, Office Action dated Jul. 1, 2016 in U.S. Appl. No. 13/804,955.
USPTO, Final Office Action dated Nov. 3, 2016 in U.S. Appl. No. 13/804,955.
USPTO, Notice of Allowance dated Jan. 19, 2017 in U.S. Appl. No. 13/804,955.
USPTO, Office Action dated Apr. 9, 2015 in U.S. Appl. No. 13/826,367.
USPTO, Final Office Action dated Jun. 26, 2015 in U.S. Appl. No. 13/826,367.
USPTO, Advisory Action dated Aug. 20, 2015 in U.S. Appl. No. 13/826,367.
USPTO, Office Action dated Oct. 2, 2015 in U.S. Appl. No. 13/826,367.
USPTO, Final Office Action dated Mar. 11, 2016 in U.S. Appl. No. 13/826,367.
USPTO, Advisory Action dated May 27, 2016 in U.S. Appl. No. 13/826,367.
USPTO, Office Action dated Jul. 1, 2016 in U.S. Appl. No. 13/826,367.
USPTO, Final Office Action dated Nov. 3, 2016 in U.S. Appl. No. 13/826,367.
USPTO, Notice of Allowance dated Dec. 28, 2016 in U.S. Appl. No. 13/826,367.
USPTO, Notice of Allowance dated Jan. 10, 2020 in U.S. Appl. No. 15/461,294.
USPTO, Notice of Allowance dated May 12, 2021 in U.S. Appl. No. 16/778,348.
USPTO, Restriction/Election Requirement dated Sep. 22, 2022 in U.S. Appl. No. 16/785,024.
USPTO, Notice of Allowance dated Oct. 19, 2022 in U.S. Appl. No. 16/785,024.
USPTO, Notice of Allowance dated Nov. 2, 2022 in U.S. Appl. No. 16/785,097.
Blass et al, "Tracker: Security and Privacy for RFID-based Supply Chains" (Feb. 6-9, 2011, 18th Annual Network Distributed System Security Symposium, pp. 1-20).
Kerschbaum and Oertel "Privacy-Preserving Pattern Matching for Anomaly Detection in RFID Anti-Counterfeiting" (2010 In Proceeding of the Workshop on RFID Security RFID sec'10 pp. 1-16).
EPCIS and CBV Implementation Guideline, "Using EPCIS and CBV standards to gain visibility of business processes Release 1.2., Ratified, Feb. 2017" (Year: 2017).

* cited by examiner

Concepts – Event Visibility

| Publisher | Event | Event Type | Mfg-A Visibility | Dist-B Visibility | Retail-C Visibility |
|---|---|---|---|---|---|
| Mfg-A | e1 | Commissioning (312) | FULL | Redacted | Redacted |
| Mfg-A | e3 | Aggregation (314) | FULL | Redacted | Redacted |
| Mfg-A | e4 | Shipping (316) | FULL | FULL | Redacted |
| Dist-B | e5 | Receiving (322) | FULL | FULL | Redacted |
| Dist-B | e6 | Disaggregation (324) | Redacted | FULL | Redacted |
| Dist-B | e7 | Shipping (326) | Redacted | FULL | FULL |
| Retail-C | e9 | Receiving (332) | Redacted | FULL | FULL |

Product History

| Product Number | Date | Event Sequence State | Location | Business Step | Disposition |
|---|---|---|---|---|---|
| sgtin 011122.999888.524 | 10/30/2012 | Consistent | n/a | disaggregation | n/a |

Drug Information

ID: 1122299888
Brand Name: BRANDNAME1
Generic Name: EVEROLIMUS
Label Name: LABELNAME1
Package Description: BLIST PACK
Package Size: 60
Drug Strength: 0.5 MG
Package Quantity:
Drug Form: TABLET
Classification: IMMUNOSUPPRESSIVES

Chain of Custody

| | | |
|---|---|---|
| commissioning | 10/18/2012 09:20:25 AM | sgtin 011122.00001.0 |
| aggregation | 10/18/2012 11:22:16 AM | sgtin 011122.00002.0 |
| shipping | 10/18/2012 01:24:07 AM | sgtin 011122.00002.0 |
| receiving | 10/20/2012 09:26:54 AM | sgtin 022233.00003.0 |
| disaggregation | 10/21/2012 09:27:07 AM | |
| aggregation | 10/25/2012 09:27:37 AM | |
| shipping | 10/27/2012 09:27:42 AM | |
| receiving | 10/27/2012 11:28:32 AM | |
| disaggregation | 10/30/2012 07:27:44 AM | |

Manufacturer View

FIGURE 11

Product History

| Product Number | Date | Event Sequence State | Location | Business Step | Disposition |
|---|---|---|---|---|---|
| sgtin 0111222.999888.524 | 10/30/2012 | Consistent | n/a | disaggregation | n/a |

Drug Information

ID: 1122229888
Brand Name: BRANDNAME1
Generic Name: EVEROLIMUS
Label Name: LABELNAME1
Package Description: BLIST PACK
Package Size: 60
Drug Strength: 0.5 MG
Package Quantity:
Drug Form: TABLET
Classification: IMMUNOSUPPRESSIVES

Chain of Custody

| | | | |
|---|---|---|---|
| commissioning | 10/18/2012 09:20:25 AM | | sgin 0111222.00001.0 |
| aggregation | 10/18/2012 11:22:16 AM | | sgin 0111222.00002.0 |
| shipping | 10/18/2012 01:24:07 AM | | sgin 0111222.00002.0 |
| receiving | 10/20/2012 09:26:54 AM | | sgin 0222333.00003.0 |
| disaggregation | 10/21/2012 09:27:07 AM | | sgin 0222333.00003.0 |
| aggregation | 10/25/2012 09:27:37 AM | | sgin 0222333.00004.0 |
| Custody Check | 10/27/2012 09:27:39 AM | | Good |
| shipping | 10/27/2012 09:27:42 AM | | sgin 0222333.00004.0 |
| receiving | 10/27/2012 11:28:32 AM | | sgin 0333444.00005.4 |
| disaggregation | 10/30/2012 07:27:44 AM | | |

Distributor View

FIGURE 12

10/18/2012  09:20:25 AM    COMMISSIONING                SGLN 0111222.00001.0

Business Step: commissioning
    Disposition: active
    Container Qty: 3
    Child Product Numbers: sgtin 0111222.999888.324
                           sgtin 0111222.999888.524
                           sscc 0111222.0000000440

10/18/2012  11:22:16 AM    AGGREGATION                  SGLN 0111222.00002.0

Business Step: aggregation
    Disposition: in_transit
    Parent Product Number: sscc 0111222.0000000440
    Container Qty: 2
    Child Product Numbers: sgtin 0111222.999888.324
                           sgtin 0111222.999888.524
    Transactions: inv 0111222.00888.i123
                  po 0111222.00888.po123

10/18/2012  01:24:07 PM    SHIPPING                     SGLN 0111222.00002.0

Business Step: shipping
    Disposition: in_transit
    Container Qty: 1
    Child Product Numbers: sscc 0111222.0000000440
    Transactions: inv 0111222.00888.i123
                  po 0111222.00888.po123

Distributor View of the Manufacturing Events
FIGURE 13

| | | | |
|---|---|---|---|
| 10/20/2012 | 09:26:54 AM | RECEIVING | SGLN 0222333.00003.0 |

Business Step: receiving
                       Disposition: in_progress
                       Container Qty: 1
         Child Product Numbers: sscc 0111222.000000440
                       Transactions: inv 011122200888.i123
                                           po 01112200888.po123

| | | | |
|---|---|---|---|
| 10/21/2012 | 09:27:07 AM | DISAGGREGATION | SGLN 0222333.00003.0 |

Business Step: disaggregation
                       Disposition: in-transit
        Parent Product Number: sscc 0111222.000000440
                     Container Qty: 2
         Child Product Numbers: sgtin 0111222.999888.324
                                           sgtin 0111222.999888.524
                     Transactions: inv 011122200888.i123
                                         po 01112200888.po123

| | | | |
|---|---|---|---|
| 10/25/2012 | 09:27:37 AM | AGGREGATION | SGLN 0222333.00004.0 |

Business Step: aggregation
                       Disposition: in_transit
       Parent Product Number: sscc 0222333.000000297
                     Container Qty: 2
        Child Product Numbers: sgtin 0111222.999888.324
                                        sgtin 0111222.999888.524
                    Transactions: inv 022233300888.i456
                                      po 02223300888.po456

| | | | |
|---|---|---|---|
| 10/27/2012 | 09:27:39 AM | CUSTODY CHECK | GOOD |

Requested By: 022333000001
                        Request ID: d7c38540-204a-11e2-9395-e0f8472ad1be
               Product Number: sgtin 0111222.999888.524
                            Location: sgln 0222333.00004.0
                    Business Step: shipping
                    Custody Check: Consistent

| | | | |
|---|---|---|---|
| 10/27/2012 | 09:27:42 AM | SHIPPING | SGLN 0222333.00004.0 |

Business Step: shipping
                       Disposition: in_transit
                     Container Qty: 1
        Child Product Numbers: sscc 0222333.000000297
                    Transactions: inv 022233300888.i456
                                   po 02223300888.po456

Distributor View of its Own Events

FIGURE 14

Product History

| Product Number | Date | Event Sequence State | Location | Business Step | Disposition |
|---|---|---|---|---|---|
| Sgtin 0111222.999888.524 | 10/30/2012 | Consistent | sgtin 0333444.00005.4 | disaggregation | in_transit |

Drug Information

ID: 1112220888
Brand Name: BRANDNAME1
Generic Name: EVEROLIMUS
Label Name: LABELNAME1
Package Description: BLIST PACK
Package Size: 60
Drug Strength: 0.5 MG
Package Quantity:
Drug Form: TABLET
Classification: IMMUNOSUPPRESSIVES

Chain of Custody

| | | |
|---|---|---|
| commissioning | 10/18/2012 09:20:25 AM | sgtin 0111222.00001.0 |
| aggregation | 10/18/2012 11:22:16 AM | sgtin 0111222.00002.0 |
| shipping | 10/18/2012 01:24:07 AM | sgtin 0111222.00002.0 |
| receiving | 10/20/2012 09:26:54 AM | sgtin 0222333.00003.0 |
| disaggregation | 10/21/2012 09:27:07 AM | sgtin 0222333.00003.0 |
| aggregation | 10/25/2012 09:27:37 AM | sgtin 0222333.00004.0 |
| Custody Check | 10/27/2012 09:27:39 AM | Good |
| shipping | 10/27/2012 09:27:42 AM | sgtin 0222333.00004.0 |
| Custody Check | 10/27/2012 09:27:48 AM | Good |
| receiving | 10/27/2012 11:28:32 AM | sgtin 0333444.00005.4 |
| disaggregation | 10/30/2012 07:27:44 AM | sgtin 0333444.00005.4 |

Pharmacy View

FIGURE 15

10/29/2012 03:26:11 PM     CUSTODY CHECK     GOOD

Requested By: 03334440000009
    Request ID: 4312de20-220f-11e2-97aa-e0f8472ad1be
    Product Number: sgtin 0111222.999888.798
    Location: sgln 0333444.00005.4
    Business Step: receiving
    Custody Check: Consistent

10/29/2012 05:26:56 PM     RECEIVING     SGLN 0333444.00005.4

Business Step: receiving
    Disposition: in-progress
    Container Qty: 2
    Child Product Numbers: sscc 0111222.000000994
    Transactions: inv 0222333008888.i456
    po 0222333008888.po456

11/01/2012 01:26:08 PM     DISAGGREGATION     SGLN 0333444.00005.4

Business Step: disaggregation
    Disposition: in_transit
    Parent Product Number: sscc 0111222.000000994
    Container Qty: 2
    Child Product Numbers: sgtin 0111222.999888.411
    sgtin 0111222.999888.798
    Transactions: inv 0222333008888.i456
    po 0222333008888.po456

Pharmacy View of Pharmacy Events

FIGURE 16

| | | | |
|---|---|---|---|
| 10/20/2012 | 03:18:49 PM | COMMISSIONING | SGLN 0111222.00001.0 |

Business Step: commissioning
Disposition: active
Container Qty: 3
Child Product Numbers: sgtin 0111222.999888.411
sgtin 0111222.999888.798
sscc 0111222.0000000994

| | | | |
|---|---|---|---|
| 10/20/2012 | 05:20:40 PM | AGGREGATION | SGLN 0111222.00002.0 |

Business Step: aggregation
Disposition: in_transit
Parent Product Number: sscc 0111222.0000000994
Container Qty: 2
Child Product Numbers: sgtin 0111222.999888.411
sgtin 0111222.999888.798
Transactions: inv 01122200888.i123
po 01122200888.po123

| | | | |
|---|---|---|---|
| 10/20/2012 | 07:22:31 PM | SHIPPING | SGLN 0111222.00002.0 |

Business Step: shipping
Disposition: in_transit
Container Qty: 1
Child Product Numbers: sscc 0111222.0000000994
Transactions: inv 01122200888.i123
po 01122200888.po123

| | | | |
|---|---|---|---|
| 10/22/2012 | 03:25:18 PM | RECEIVING | SGLN 0222333.00003.0 |

Business Step: receiving
Disposition: in_progress
Container Qty: 1
Child Product Numbers: sscc 0111222.0000000994
Transactions: inv 01122200888.i123
po 01122200888.po123

| | | | |
|---|---|---|---|
| 10/27/2012 | 11:26:06 AM | SHIPPING | SGLN 0222333.00004.0 |

Business Step: shipping
Disposition: in_transit
Container Qty: 1
Child Product Numbers: sscc 0111222.0000000994
Transactions: inv 02223330888.i456
po 02223330888.po456

Pharmacy View

FIGURE 17

| Product Number | Location | Assessment | Disposition | Time |
|---|---|---|---|---|
| sgtin 0111222.999888.434 | OK | Consistent | in_progress | 04/03/2010 |
| sgtin 0111222.999888.427 | TX | Consistent | in_progress | 04/05/2010 |
| sgtin 0111222.999888.855 | CO | Consistent | active | 04/01/2010 |
| sgtin 0111222.999888.162 | OK | Consistent | in_progress | 04/03/2010 |
| sgtin 0111222.999888.114 | CO | Consistent | active | 04/01/2010 |
| sgtin 0111222.999888.209 | TX | Consistent | in_progress | 04/05/2010 |
| sgtin 0111222.999888.671 | OK | Consistent | in_progress | 04/03/2010 |
| sgtin 0111222.999888.535 | OK | Consistent | in_progress | 04/03/2010 |
| sgtin 0111222.999888.254 | OK | Consistent | in_progress | 04/03/2010 |

Lot Report

FIGURE 18

Product History

| Product Number | Date | Event Sequence State | Location | Business Step | Disposition |
|---|---|---|---|---|---|
| Sgtin 011122.999888.524 | 10/28/2012 | Recalled | n/a | holding | non_sellable_recalled |

Chain of Custody

| | | | |
|---|---|---|---|
| commissioning | 10/07/2012 07:59:41 AM | | sgtin 011122.00001.0 |
| aggregation | 10/13/2012 08:05:02 AM | | sgtin 011122.00002.0 |
| shipping | 10/27/2012 08:03:11 AM | | sgtin 011122.00002.0 |
| Custody Check | 10/28/2012 07:59:42 AM | | Good |
| receiving | 10/28/2012 07:59:46 AM | | sgtin 022233.00003.0 |
| holding | 10/28/2012 07:59:48 AM | | |
| Custody Check | 10/28/2012 08:00:02 AM | | Bad |

Drug Information

ID: 11222299888
Brand Name: BRANDNAME1
Generic Name: EVEROLIMUS
Label Name: LABELNAME1
Package Description: BLIST PACK
Package Size: 60
Drug Strength: 0.5 MG
Package Quantity:
Drug Form: TABLET
Classification: IMMUNOSUPPRESSIVES

FIGURE 19

| | | | |
|---|---|---|---|
| 10/07/2012 | 07:59:41 AM | COMMISSIONING | SGLN 0111222.00001.0 |

Business Step: commissioning
Disposition: active
Container Qty: 12
Child Product Numbers: sgtin 0111222.999888.001
sgtin 0111222.999888.0010
sgtin 0111222.999888.0011
sgtin 0111222.999888.0012
sgtin 0111222.999888.002
sgtin 0111222.999888.003
sgtin 0111222.999888.004
sgtin 0111222.999888.005
sgtin 0111222.999888.006
sgtin 0111222.999888.007
sgtin 0111222.999888.008
sgtin 0111222.999888.009

| | | | |
|---|---|---|---|
| 10/13/2012 | 08:05:02 AM | AGGREGATION | SGLN 0111222.00002.0 |

Business Step: aggregation
Disposition: in-progress
Parent Product Number: sscc 0111222.0000000001
Container Qty: 12
Child Product Numbers: sgtin 0111222.999888.001
sgtin 0111222.999888.0010
sgtin 0111222.999888.0011
sgtin 0111222.999888.0012
sgtin 0111222.999888.002
sgtin 0111222.999888.003
sgtin 0111222.999888.004
sgtin 0111222.999888.005
sgtin 0111222.999888.006
sgtin 0111222.999888.007
sgtin 0111222.999888.008
sgtin 0111222.999888.009
Transactions: inv 011122200888.i123
po 02223300888.po123

| | | | |
|---|---|---|---|
| 10/27/2012 | 08:03:11 AM | SHIPPING | SGLN 0111222.00002.0 |

Business Step: shipping
Disposition: in_transit
Container Qty: 1
Child Product Numbers: sscc 0111222.000000001
Transactions: inv 011122200888.i123
po 011122200888.po123

FIGURE 20

10/28/2012  07:59:42 AM   CUSTODY CHECK   GOOD
               Requested By: 022233000001
                 Request ID: b8b9acc0-2107-11e2-97aa-e0f8472ad1be
          Product Number: sgtin 0111222.999888.001
                    Location: sgln 0222333.00000.0
                Business Step: receiving
               Custody Check: Consistent 10/28/2012  07:59:46 AM   RECEIVING   SGLN 0222333.00003.0
                Business Step: receiving
                  Disposition: in_progress
                Container Qty: 1
      Child Product Numbers: sscc 0111222.0000000001
                  Transactions: inv 011122200888.i123
                                      po 022233300999.po123

10/28/2012  07:59:48 AM   HOLDING   N/A
                Business Step: holding
                  Disposition: non-sellable-recalled
                Container Qty: 12
      Child Product Numbers: sgtin 0111222.999888.001
                                      sgtin 0111222.999888.0010
                                      sgtin 0111222.999888.0011
                                      sgtin 0111222.999888.0012
                                      sgtin 0111222.999888.002
                                      sgtin 0111222.999888.003
                                      sgtin 0111222.999888.004
                                      sgtin 0111222.999888.005
                                      sgtin 0111222.999888.006
                                      sgtin 0111222.999888.007
                                      sgtin 0111222.999888.008
                                      sgtin 0111222.999888.009

10/28/2012  08:00:02 AM   CUSTODY CHECK   BAD
               Requested By: 022233000001
                 Request ID: c4973df0-2107-11e2-97aa-e0f8472ad1be
          Product Number: sgtin 0111222.999888.001
                    Location: sgln 0222333.00000.0
                Business Step: shipping
               Custody Check: Recalled - RecalledEvent

FIGURE 21

SHIPPING EVENTS AND RECEIVING EVENTS

CROSS-REFERENCE TO RELATED APPLICATIONS

This application is a continuation of, claims priority to and the benefit of, U.S. Ser. No. 16/785,097, filed Feb. 7, 2020 and entitled SHIPPING EVENTS AND RECEIVING EVENTS. The '097 application is a continuation of, claims priority to and the benefit of, U.S. Ser. No. 16/778,348, filed Jan. 31, 2020 and entitled SUPPLY CHAIN EVENT MANAGEMENT, and issued as U.S. Pat. No. 11,042,830 on Jun. 22, 2021. The '348 application is a continuation of, claims priority to and the benefit of U.S. Ser. No. 15/461,294 filed Mar. 16, 2017 and entitled SUPPLY CHAIN EVENT MANAGEMENT, and issued as U.S. Pat. No. 10,592,848 on Mar. 17, 2020. The '294 application is a continuation of, claims priority to and the benefit of U.S. Ser. No. 13/804,955 filed Mar. 14, 2013 and entitled SYSTEMS AND METHODS FOR SUPPLY CHAIN MANAGEMENT, and issued as U.S. Pat. No. 9,633,325 on Apr. 25, 2017. The '955 is a continuation of, claims priority to and the benefit of, U.S. Ser. No. 13/804,572 filed on Mar. 14, 2013 entitled SYSTEMS AND METHODS FOR SUPPLY CHAIN MANAGEMENT, and issued as U.S. Pat. No. 9,589,247 on Mar. 7, 2017. The '572 application claims priority to, and is a non-provisional of, U.S. Provisional No. 61/725,350 filed on Nov. 12, 2012. All of the aforementioned applications are incorporated herein by reference in their entirety.

FIELD

Various embodiments are directed to systems and methods for supply chain management, and more particularly, to tracking, tracing, authenticating, and reporting supply chain events for healthcare products.

BACKGROUND

Securing the supply chain is one of the most important challenges confronting manufacturers and other entities involved in supplying products to the healthcare industry. State and federal legislation require the implementation of pedigree and tracking systems with the goal of enhancing patient safety by helping to secure the supply chain.

The high number of products in a supply chain makes it difficult to track individual products or groups of products (e.g. a "case"). In addition, the number of different parties (e.g., manufacturer, distributor, pharmacy and hospital) adds to the complexity of tracking products.

Additionally, due to the high volume of products in a supply chain, counterfeit goods are often prevalent. Counterfeiters typically generate duplicate packaging and submit the fake product into a distributor's warehouse. This will result in the distributor unknowingly shipping real and counterfeit items. Various embodiments of the present disclosure help resolve such issues in an efficient manner.

BRIEF DESCRIPTION OF THE DRAWINGS

A more complete understanding of the various embodiments may be derived by referring to the detailed description and claims when considered in connection with the following illustrative figures:

FIGS. 3-7 illustrate exemplary partners generating and publishing events, according to various embodiments.

FIGS. 11-21 illustrate exemplary screenshots, according to various embodiments.

DETAILED DESCRIPTION

Exemplary System

Figure 1:
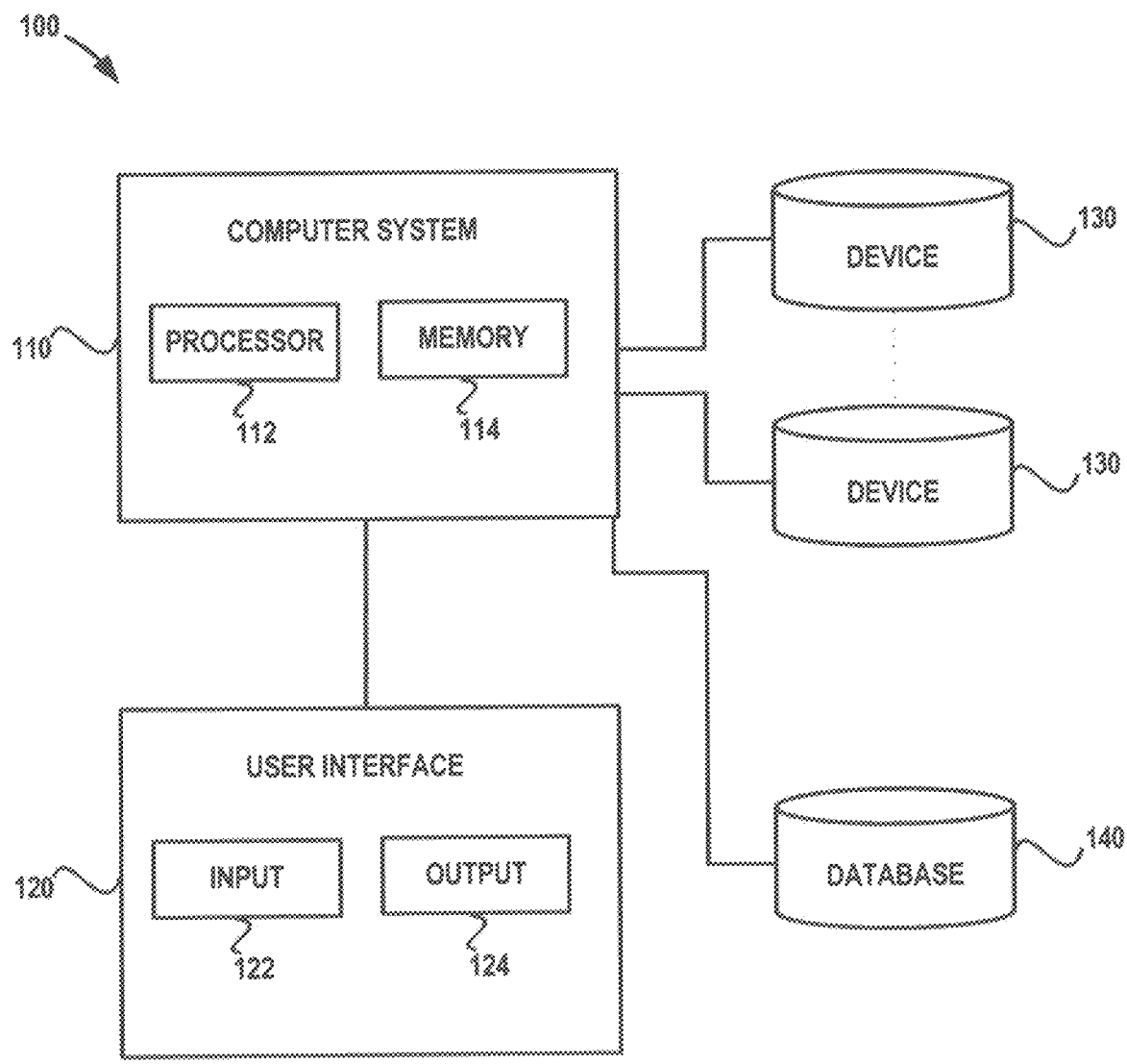
FIG. 1 illustrates an exemplary system, according to various embodiments.

An exemplary system 100 is depicted in FIG. 1. In various embodiments, the system 100 includes a computer system 110 comprising a processor 112 and a memory 114. Computer system 110 is in communication with a user interface 120, which includes an input device 122, and output device 124. Computer system 110 is further in communication with multiple external devices 130, as well as a database 140. System 100 may be implemented in a facility for tracking and tracing products, and may be one of a plurality of such systems operating together, or separately, to locate products, and/or provide information on the products to the appropriate parties. Such stations may share any of the devices or resources shown in FIG. 1.

In various embodiments, and as shown in FIG. 1, computer system 110 may store a software program configured to perform the methods described herein in the memory 114, and run the software program using the processor 112. The computer system 110 may include any number of individual processors 112 and memories 114. Various data may be communicated between the computer system 110 and a user via the user interface 120. Such information may also be communicated between the computer system 110 and the external devices 130, database 140, and/or any other computing device connected to the computer system 110 (e.g., through any network such as a local area network (LAN), or wide area network (WAN) such as the Internet).

In exemplary system 100 depicted in FIG. 1, the processor 112 retrieves and executes instructions stored in the memory 114 to control the operation of the computer system 110. Any number and type of processor(s) (e.g., an integrated circuit microprocessor, microcontroller, and/or digital signal processor (DSP)), can be used in conjunction with the various embodiments. The processor 112 may include, and/or operate in conjunction with, any other suitable components and features, such as comparators, analog-to-digital converters (ADCs), and/or digital-to-analog converters (DACs). Functionality of various embodiments may also be implemented through various hardware components storing machine-readable instructions, such as application-specific integrated circuits (ASICs), field-programmable gate arrays (FPGAs) and/or complex programmable logic devices (CPLDs).

The memory 114 may include a non-transitory computer-readable medium (such as on a CD-ROM, DVD-ROM, hard drive or FLASH memory) storing computer-readable instructions stored thereon that can be executed by the processor 112 to perform the methods of the present disclosure. The memory 114 may include any combination of different memory storage devices, such as hard drives, random access memory (RAM), read only memory (ROM), FLASH memory, or any other type of volatile and/or non-volatile memory.

The computer system 110 may receive and display information (such as information related to specific products) via the user interface 120. The user interface 120 (and the user interfaces of any external devices 130 used in conjunction with various embodiments) may include various peripheral output devices 124 (such as monitors and printers), as well as any suitable input or control devices 122 (such as a mouse and keyboard) to allow users to control and interact with the software program.

The user interface 120 may include any number of components, devices, and/or systems (e.g., speakers, an external memory device, a touch pad, a touch screen, and/or an alphanumeric keypad) to allow a user to enter instructions, data related to products (e.g., problem products), and other input. The user interface 120 may also include a microphone to allow a user to provide audio input, as well as a camera to allow the user to capture still or video images of a product being analyzed. Any of the components of the user interface 120 may be utilized as external devices 130 as described below.

The user interface of any component operating in conjunction with various embodiments may include, or operate with, audio or speech recognition software to process and analyze audio or verbal input through the user interface, as well as pattern recognition software to analyze graphics, text, and video received through the user interface 120, from the external devices 130, or from any other source.

The computer system 110 may communicate with any number of devices 130. In various embodiments, one or more devices 130 are configured to obtain information regarding a particular product and provide the information to the computer system 110 through a wired or wireless connection. Devices 130 may also communicate directly with the database 140, each other, or with any other system or device operating in conjunction with the embodiments described herein.

Various embodiments can track and trace items in a supply chain via an electronic product code (EPC). The EPC can be any code, symbol, picture and/or any other unique identifier assigned to each item or subset of items in the chain. EPCs and other information regarding a product may be stored in a barcode, QR code, radio frequency identification (RFID) tag or any other method or system for identifying an item. The EPC may be attached to the product's packaging, and/or associated with a product in any other desired manner. Accordingly, various embodiments may operate in conjunction with a device 130 that includes a handheld scanner (e.g., a barcode scanner and/or RFID reader) for reading such information and communicating it to the computer system 110, database 140, or other system. Such scanners may communicate with the computer system 110 or other device through a wired connection, such as a universal serial bus (USB) connection, a computer network connection, a mobile device synchronization port connection, a power connection, a security cable and/or any other means set forth herein or known in the art. Such scanners may also communicate with any device operating in conjunction with the system through any desired wireless connection or network, such as a wireless Internet connection, a cellular telephone network connection, a wireless LAN connection, a wireless WAN connection, and/or an optical connection. Various embodiments may include, or operate in conjunction with, any other type of scanner or similar device.

The database 140 stores and provides information related to products, as well as any other desired information (as further discussed herein). The database 140 may be implemented on computer system 110 or hosted by another system or device (such as a server) in communication with the computer system 100 via, for example, a network such as a LAN or WAN. In various embodiments, database 140 may be implemented as a relational database.

The computer system 110 may include, or operate in conjunction with, any type of computing device, such as a laptop computer, a desktop computer, a mobile subscriber communication device, a mobile phone, a personal digital assistant (PDA), a tablet computer, a digital camera, a video camera, a video game console, and/or a media player.

As set forth herein, the computer system 110 and other computing devices operating in conjunction with various embodiments may include an operating system (e.g., Windows, OS2, UNIX, Linux, Solaris, MacOS, etc.) as well as various conventional support software and drivers typically associated with computers. Software applications stored in the memory of such devices may be entirely or partially served or executed by the processor(s) in performing methods or processes of the present disclosure.

Any of the components in FIG. 1, as well as other systems and components operating with, or as part of, various embodiments may communicate with each other via a network (not shown). In various embodiments, one or more components of system 100 may include a wireless transceiver and the network may comprise a wireless system to allow wireless communication between various systems and devices, such as a wireless mobile telephony network, General Packet Radio Service (GPRS) network, wireless Local Area Network (WLAN), Global System for Mobile Communications (GSM) network, Personal Communication Service (PCS) network, Advanced Mobile Phone System (AMPS) network, and/or a satellite communication network. Such networks may be configured to facilitate communication via any other type of connection, such as a wired Internet connection, a wireless Internet connection, a cellular telephone network connection, a wireless LAN connection, a wireless WAN connection, an optical connection, a USB connection, and/or a mobile device synchronization port connection.

Event Sequence Introduction

Various embodiments provide a comprehensive solution to capture, correlate and/or assess supply chain events, and to track and trace such events across any portion of the supply chain and/or the entire supply chain. The disclosure includes forward and/or reverse logistics with appropriate data visibility governance. Various embodiments also provide pedigree and/or chain of custody support for prevention and/or early detection of fraud or other anomalies in the supply chain. Various embodiments also provide alerting and/or notification of abnormalities and/or suspicious events. Various embodiments provide metrics and/or analytics for insights and improvements to the systems and methods. The embodiments disclosed herein can also be configured to provide efficient and effective support for supply chain members, while remaining adaptive to changing regulatory and legal requirements.

As described in more detail herein, various embodiments of the disclosure may create, store, process, and/or retrieve sets of events associated with one or more EPCs. Various embodiments can help detect and/or prevent acts of fraud, missing items in a supply chain, missing events associated with such items, duplicate packaging of items, and/or other issues that are difficult or impossible for conventional supply management systems to identify.

In various embodiments, sets of events for one or more EPCs may be time-ordered in a sequence, also referred to herein as an "event sequence." An EPC used in conjunction with various embodiments may be in any desired format. For example, the EPC for an item may include a global trade item number (GTIN) and/or national drug code (NDC) that helps describe the item. EPCs may include any combination of alphanumeric characters, symbols, graphics, or other identifiers. In various embodiments, an EPC may include a header, filter value, partition value, EPC manager number (e.g., UPC company prefix), GTIN item reference number, and/or a serial number. An EPCIS event may include any desired information, such as the EPC, name, manufacturer, dosage form, strength, container size, lot number, name of trading partners, shipping addresses, a global location number (GLN), licenses, and/or other information associated with a product.

An EPC may be assigned to one or more products at the "unit of sale" level, also known as a "sellable unit" or the "lowest unit of sale." As used herein, the "unit of sale" level is the smallest individual unit of product that can be offered for sale to a pharmacy, such as a bottle of pills, or a package containing multiple vials. Various embodiments can track products at any level of aggregation (including products packaged inside multiple levels of nested containers) such as: bundles, trays, cases, totes, pallets, inner packs, wallets, and overpack boxes. The relationship between sellable units and their various aggregations can be stored in the external data repository. Storage of events may also be persistent such that the chain of custody of an item or package can be traced even after an aggregated container is decommissioned.

Various embodiments can follow individual unit of sale-level products (or groups thereof) based on events associated with the products. Various embodiments may operate in conjunction with any type of event associated with a product in a supply chain. As discussed above, an EPC is a unique identifier corresponding to a specific tangible item in a supply chain, and events may include any state (or change therein) associated with the item. Various embodiments may be used to receive, store, and analyze data regarding items shipped in any manner, including homogeneous shipments, mixed-case shipments, partial cases, shipments with or without pallets, drop shipments, and shipments in totes.

Different entities of the supply chain may participate and utilize various embodiments of the disclosure. These entities include, but are not limited to, manufacturers, third party manufacturers, wholesalers, repackaging facilities, third party logistic providers, reverse distributors, retailers, pharmacies, and provider (e.g. hospital) pharmacies.

For example, a manufacturer trading partner in a supply chain may generate and/or publish "commissioning" events as an initiating event for a sellable item. The commissioning event is used to identify sellable items, as well as their containers (e.g., cases, pallets, and totes) or aggregation hierarchies (lots) to the system. While manufacturers may normally initiate commissioning events, other members of the supply chain may generate commissioning events, as well as any other suitable type of event. For example, wholesalers may publish commissioning events when they repackage units and/or create kits.

Commissioning events can be published to the external data repository, with each event containing an identifier (such as a serial number) for the commissioned item or container. The commissioning event may include any other desired information, including an event date/time (timestamp), a record time (the time the event was written to the participant's data system), an EPC List (names the physical object(s) to which the event pertains, for example, a container), a read point (GLN), a business location (GLN), a lot/batch number, a lot/batch expiration date, a GTIN, drug product information, a Manufacturer Name or Information Provider Name, a Manufacturer or Information Provider GLN, and contact information for a Manufacturer or Information Provider.

In various embodiments, commissioning of items is a separate event from the commissioning of containers, and there should be only one commissioning event for an item from a manufacturer, either at the Third Party Manufacturer or at the NDA brand owner's manufacturing site. Normally, a commissioning event is expected prior to a shipment event. In addition, duplicate commissioning events may be indicative of fraud or duplicate products in the supply chain. Trading partners downstream from the manufacturer or issuer of the commissioning event may look for commissioning events prior to shipment events for the same item.

Rules from a rules engine may be enforced on commissioning events (as with other events). For example, various embodiments may include that, in response to the item having a commissioning event associated to it (if not previously decommissioned), a new commissioning event is not allowed. For example, various embodiments may include that, in response to the item having a commissioning event associated to it (if not previously decommissioned), new commissioning events are accepted but reported as suspect. Various embodiments may also issue a warning on a shipping event for an item that was never commissioned.

However, systems and methods of the disclosure may also be configured to be flexible enough to allow commissioning to occur at varying steps of the process. For example, a product may be commissioned on the production line, as a shipment is being packed, and/or by a wholesaler (e.g., commissioning a container).

A "decommissioning" event may be issued in response to a number of scenarios, such as the destruction of unconsumed, expired, and/or damaged product; recalled products at the point of destruction; a product being dispensed or consumed; and/or a container being discarded. A decommissioning event can occur at any point in the event chain.

In various embodiments, even after a container is "decommissioned," the data repository may still maintain the commissioning and aggregation data for the container, so that at a future date it is possible to determine what container originally held (and was associated to) a specific sellable item. The data repository in various embodiments may accept such decommissioning and disaggregation events if published, and can auto-generate decommissions if desired.

Various embodiments may utilize "aggregation events" that describe relationships between items having EPCs. For example, an aggregation event may include adding six bottles of aspirin (each with its own EPC) into a shipping container (also with its own EPC). Various embodiments may register the aggregation event and track the six bottles individually or via the shipping container in which they reside.

Aggregation event data that documents chain of custody may be made available to all downstream participants with appropriate data rights. Various embodiments may allow multiple aggregation events for one sellable item within the supply chain, such as where a manufacturer aggregates an item to a case, then a wholesaler disaggregates the item from the case, and re-aggregates the item to a tote. Aggregated container serial numbers may also re-used for reusable containers (such as totes) to accommodate situations where some reusable containers serial numbers never change, while others do.

Various embodiments can track products at various possible levels of aggregation including: individual items, bundle, tray, case, tote, pallet, inner pack, wallet, and overpack box. It will be appreciated that this is an exemplary list of various levels of aggregation, and other levels of aggregation are possible, including: shipping product in homogenous cases or other level of container, shipping product in mixed cases or other level of container, shipping product in partial cases or other level of container, shipping product with or without pallets, and shipping product via drop shipment.

A "disaggregation event" may include removing some of the items (e.g., bottles of aspirin) from a container. Other events may capture business processes, such as shipping, receiving, dispensing, and/or holding a shipment for return. Various embodiments may operate in conjunction with any type of events, including those described in the GS1 Electronic Product Code Information Services (EPCIS) standard. Systems and methods may further receive decommissioning events from members of a supply chain. Various embodiments may also be configurable to automatically generate decommissioning events on behalf of participants who choose to use this functionality.

Figure 2:
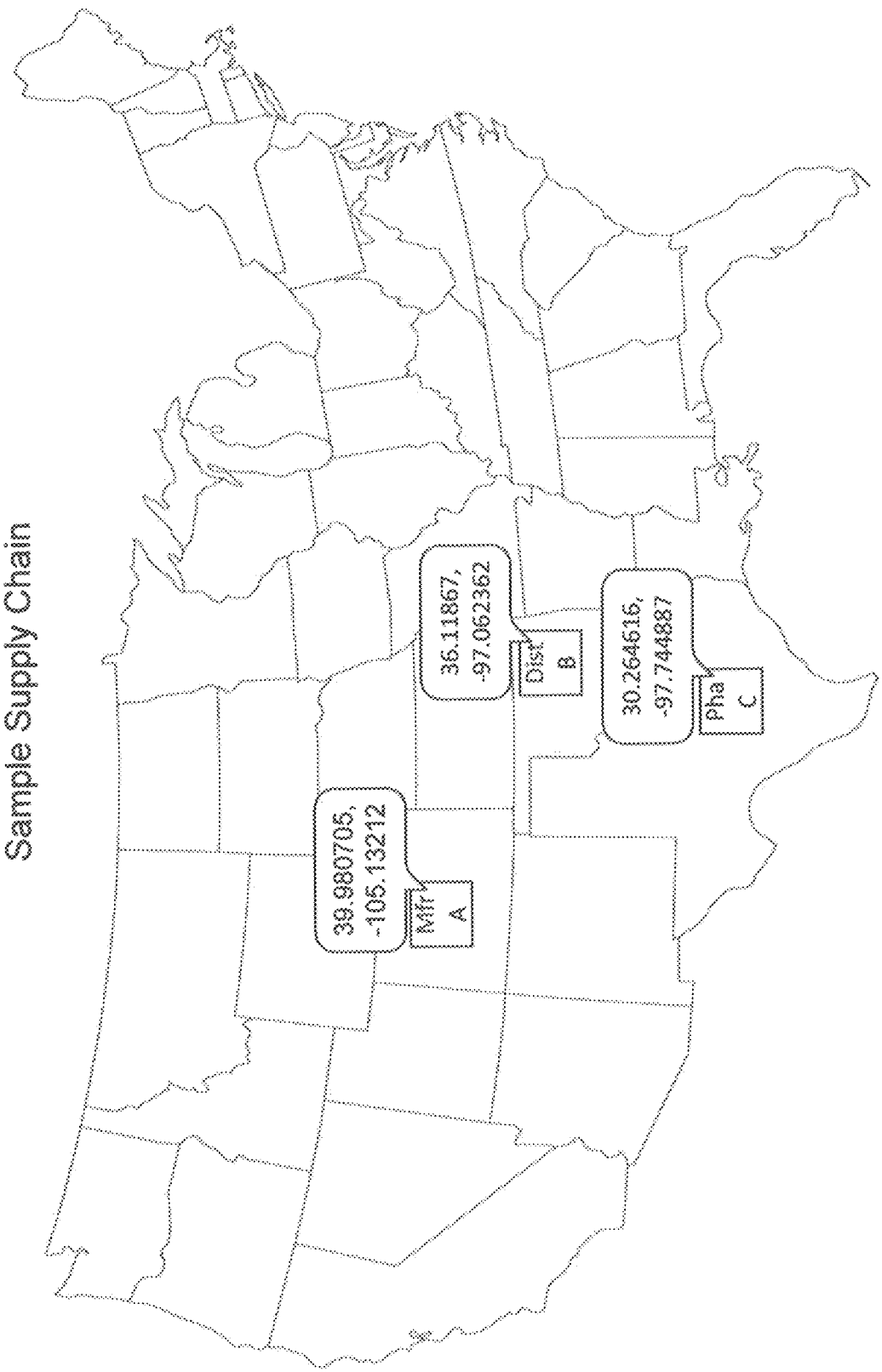
FIG. 2 illustrates exemplary partners in an exemplary supply chain, according to various embodiments.
Figure 3:
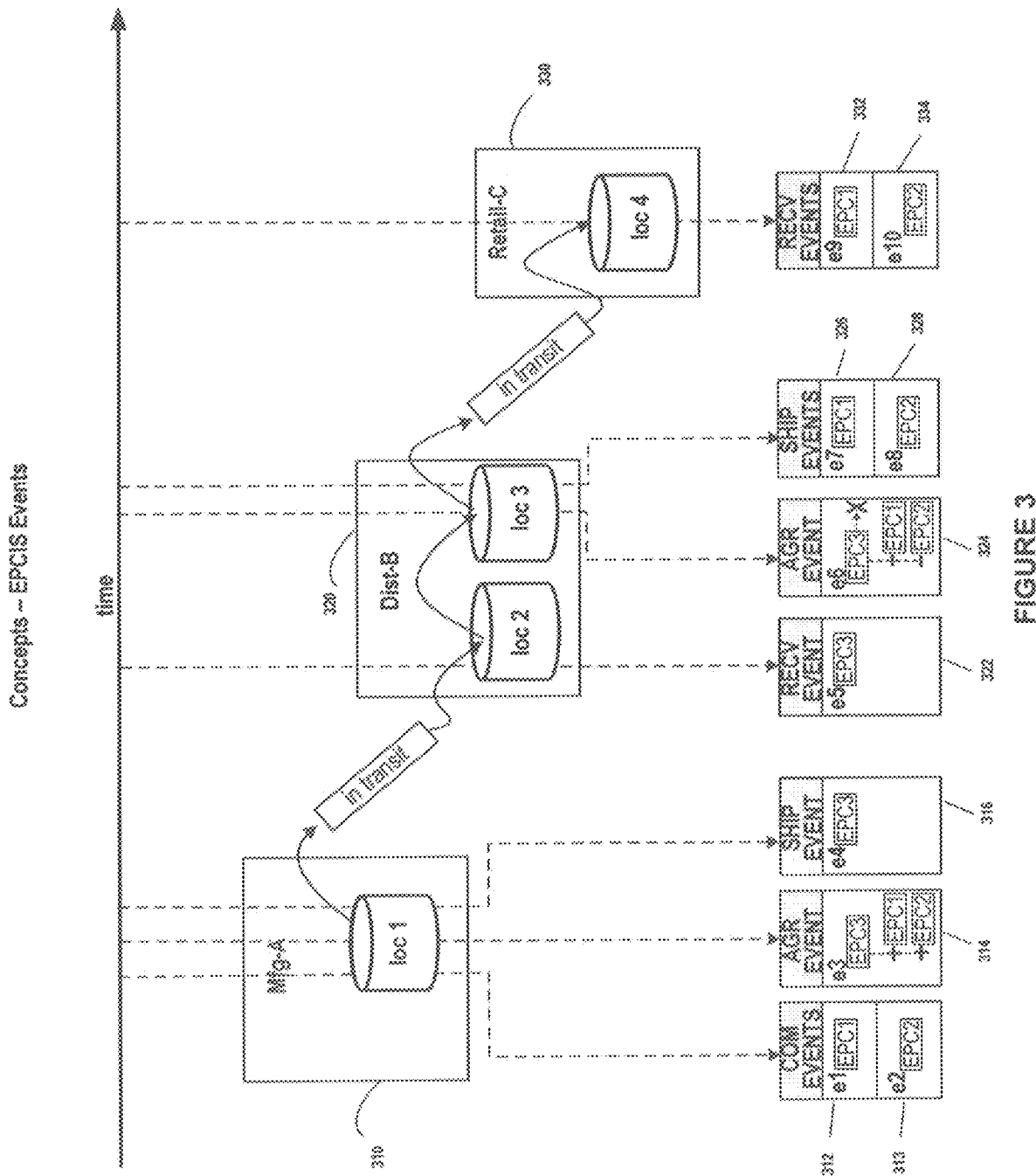

FIG. 2 depicts different partners in an exemplary supply chain (manufacturers, wholesalers, pharmacies, etc.) that would utilize various embodiments of systems and methods of the present disclosure. In this example, Manufacturer A, Distributor B, and Pharmacy C each connect via an external data repository. The external data repository may include one or more servers and may communicate with databases and computer systems local to each trading partner, and may be referred to herein as the "external data repository server(s)."

The following includes examples of event handling associated with the disclosed embodiments. As will be appreciated, examples disclosed herein are only exemplary examples and are not intended to fully document all scenarios.

Event Handling

Handling Commissioning Events

In response to the system receiving a commissioning event from an entity in the supply chain, the commissioning event may be handled in the following manner by various embodiments. For each EPC listed within the commissioning event, the system determines whether the EPC is known. If the EPC is not known, then the system records the EPC and stores the EPC information in the repository. The system then associates the commissioning event with the EPC, whether or not the EPC was previously known.

For each associated EPC, the system determines whether an event sequence exists for the EPC. If an event sequence exists, the system may perform a preliminary assessment of the event sequence relative to this commissioning event as follows. If an event sequence does not exist, the system initiates an EPC event sequence with the commissioning event as the initial event for the EPC.

In accordance with various embodiments, for assessing an EPC event sequence, when the current event is a commissioning event, the system checks to see if there are any events in the event sequence earlier than the current commissioning event. If there are earlier events in the event sequence for the EPC, the system sets the EPC state to a potential duplicate EPC condition, as the commissioning event should be the first event.

For each associated EPC, if the current EPC state indicates a missing commissioning event for the event sequence, the system determines whether the current commissioning event satisfies the missing commissioning event. If the current commissioning event satisfies the missing commissioning event, the system clears the EPC state of the missing commissioning event. If the missing commissioning event state for the EPC cannot be cleared by the current commissioning event, the missing commissioning event state is updated to reflect the presence of a commissioning event that does not satisfy the previous missing commissioning event state.

Handling Aggregation Events

In response to the system receiving an aggregation event from an entity in the supply chain, the aggregation event may be handled in the following manner by various embodiments. For the parent EPC listed within the aggregation event, the system determines whether the parent EPC is known. If the parent EPC is not known, the system records the parent EPC and stores the parent EPC information in the repository. The system then associates the aggregation event with the parent EPC, whether the parent EPC was previously known or not.

For each child EPC listed within the aggregation event, the system determines whether the child EPC is known. If the child EPC is not known, the system records the child EPC and stores the child EPC information in the repository. The system then associates the aggregation event with the child EPC, whether the child EPC was previously known or not.

For the parent EPC, the system determines whether an event sequence exists for the parent EPC. If an event sequence exists, the system may perform a preliminary assessment of the event sequence relative to this aggregation event as follows. If an event sequence does not exist, the system initiates an EPC event sequence for the parent EPC.

In accordance with various embodiments, the preliminary assessment of the parent EPC event sequence may include:

If a decommissioning event exists earlier in the event sequence, then the system sets the parent EPC state to a condition reflecting error as there should not be any events after a decommissioning event.

If the parent EPC container is not reusable, then the system should check for any disaggregation events earlier in the event sequence than the current aggregation event. If a disaggregation event exists for the parent EPC container, then the system sets the parent EPC state to a condition reflecting error as a non-reusable container as a parent should not previously been involved in disaggregation.

If the parent EPC container is not reusable, then the system should check for any shipping or receiving events earlier in the event sequence than the current aggregation event. If a shipping or receiving event exists for the parent EPC container, then the system sets the parent EPC state to a condition reflecting error, as a non-reusable container cannot not be shipped or received and then more products added.

If the parent EPC container is not reusable, then the system should check that there is only one commissioning event earlier in the event sequence than the current event. If there is more than one commissioning event, then the system sets the parent EPC state to a condition reflecting error as there should only be one commissioning event.

If the parent EPC event sequence has events subsequent in time to the current aggregation event, the system may associate each such subsequent event for the parent EPC with each of the child EPCs listed in the aggregation event. These subsequent events might include ship, receiving, disaggregation and/or decommissioning events. The system will only associate the ship, receiving and disaggregation events with the child EPCs. These subsequent events, when associated with the child EPCs, are applied recursively through the parent/child containment hierarchy.

For each child EPC listed in the aggregation event, the system determines whether an event sequence exists for the child EPC. If an event sequence exists, the system may perform a preliminary assessment of the event sequence relative to this aggregation event, in accordance with various embodiments, as follows. If an event sequence does not exist, the system initiates an EPC event sequence for the child EPC. If the system begins the event sequence with the aggregation event, then if the child EPC is an item, the EPC state is set to indicate a missing commissioning event as an item should have a commissioning event.

In accordance with various embodiments, the preliminary assessment of the child EPC event sequence may include:

If a decommissioning event exists earlier in the event sequence, then the system sets the child EPC state to a condition reflecting error as there should not be any events after a decommissioning event.

If the child EPC is an individual item, then the system checks for existence of only one commissioning event earlier in the event sequence then the current event. If there is more than one commissioning event, the system sets the child EPC state to a condition reflecting error as there should only be one commissioning event for an individual item.

If the child EPC is a container, whether or not the container is reusable, the system should check for any disaggregation events, in which the child EPC appears as a parent, that occur earlier in the event sequence than the current aggregation event. If a disaggregation event exists in which the child EPC appears as a parent, then the system sets the child EPC state to a condition reflecting error as an open container cannot be aggregated into another container.

If the child EPC is a container, whether or not the container is reusable, the system should check for any aggregation events, in which an EPC appears as a child, that occur earlier in the event sequence than the current aggregation event, and where the parent EPC of the earlier aggregation event is also the parent EPC of the current event. If such an event exists, then the system sets the child EPC state to a condition reflecting error as an item can only be added once to a container.

If the child EPC is a container, and the container is not reusable, then the system should check for an aggregation event earlier in the event sequence in which the child EPC appears as the parent. If such an event is not found, then the system sets the child EPC state to a condition reflecting error as a non-reusable container should have its own parent aggregation event.

If the child EPC is a container, and the container is not reusable, then the system should check that there is only one commissioning event earlier in the event sequence than the current event. If there is more than one commissioning event, then the system sets the child EPC state to a condition reflecting error as there should only be one commissioning event.

For each child EPC, if an aggregation event exists earlier in the event sequence where the child EPC is also a child of the earlier aggregation event, then the system deduces a disaggregation event for the parent EPC and for each of the child EPCs of that earlier aggregation event.

Handling Disaggregation Events

When the system receives a disaggregation event from an entity in the supply chain, the disaggregation event may be handled in the following manner by various embodiments. For the parent EPC listed within the disaggregation event, the system determines whether the parent EPC is known. If the parent EPC is not known, the system records the parent EPC and stores the parent EPC information in the repository. The system then associates the disaggregation event with the parent EPC, whether the parent EPC was previously known or not.

For each child EPC listed within the disaggregation event, the system determines whether the child EPC is known. If the child EPC is not known, the system records the child EPC and stores the child EPC information in the repository. The system then associates the disaggregation event with the child EPC, whether the child EPC was previously known or not.

For the parent EPC, the system determines whether an event sequence exists for the parent EPC. If an event sequence exists, the system may perform a preliminary assessment of the event sequence relative to this disaggregation event as follows. If an event sequence does not exist, the system initiates an EPC event sequence for the parent EPC.

In accordance with various embodiments, the preliminary assessment of the parent EPC event sequence may include:

If a decommissioning event exists earlier in the event sequence, then the system sets the parent EPC state to a condition reflecting error as there should not be any events after a decommissioning event.

For the parent EPC container (reusable or not), the system should check for the existence of at least one aggregation event earlier in the event sequence than the current aggregation event, where the parent EPC appears as a parent for the earlier aggregation event. If such an aggregation event does not exist for the parent EPC container, then the system sets the parent EPC state to a condition reflecting error as an aggregation event should exist before the current disaggregation event.

If the parent EPC container is not reusable, then the system should check that there is only one commissioning event earlier in the event sequence than the current event. If there is more than one commissioning event, then the system sets the parent EPC state to a condition reflecting error as there should only be one commissioning event.

For each child EPC listed in the disaggregation event, the system determines whether an event sequence exists for the child EPC. If an event sequence exists, the system may perform a preliminary assessment of the event sequence relative to this disaggregation event, in accordance with various embodiments, as follows. If an event sequence does not exist, the system initiates an EPC event sequence for the child EPC. If the system begins the event sequence with the current disaggregation event, then if the child EPC is an item, the EPC state is set to indicate a missing commissioning event as an item should have a commissioning event.

In accordance with various embodiments, the preliminary assessment of the child EPC event sequence may include:

If a decommissioning event exists earlier in the event sequence, then the system sets the child EPC state to a condition reflecting error as there should not be any events after a decommissioning event.

For the child EPC (item or container), the system checks for the existence of only one aggregation event earlier in the event sequence then the current event, where the child EPC appears as a child in the earlier aggregation event. If there is zero or more than one such earlier aggregation events where the child EPC appears as a child, then the system sets the child EPC state to a condition reflecting error as a child can participate in only parent/child relationship at a time.

If the child EPC is an individual item, then the system checks for existence of only one commissioning event earlier in the event sequence then the current event. If there is more than one commissioning event or no commissioning event, then the system sets the child EPC state to a condition reflecting error as there should be one (and only one) commissioning event for an individual item.

If the child EPC is a container, and the container is not reusable, then the system should check for an aggregation event earlier in the event sequence in which the child EPC appears as the parent. If such an event is not found, then the system sets the child EPC state to a condition reflecting error as a non-reusable container should have its own parent aggregation event.

If the child EPC is a container, and the container is not reusable, then the system should check that there is only one commissioning event earlier in the event sequence than the current event. If there is more than one commissioning event, then the system sets the child EPC state to a condition reflecting error as there should only be one commissioning event.

Handling Decommissioning Events

When the system receives a decommissioning event from an entity in the supply chain, the decommissioning event may be handled in the following manner by various embodiments. For each EPC listed within the decommissioning event, the system determines whether the EPC is known. If the EPC is not known, then the system records the EPC and stores the EPC information in the repository. The system then associates the decommissioning event with the EPC, whether or not the EPC was previously known.

For each associated EPC, the system determines whether an event sequence exists for the EPC. If an event sequence exists, the system may perform a preliminary assessment of the event sequence relative to this decommissioning event as follows. If an event sequence does not exist, the system initiates an EPC event sequence with the decommissioning event as the initial event for the EPC. If the EPC is for an item and the event sequence does not exist, then the system sets the EPC state to note a missing commissioning event condition. If the EPC is for a container and the event sequence does not exist, then the system sets the EPC state to note a missing aggregation event condition.

In accordance with various embodiments, for assessing an EPC event sequence, when the current event is a decommissioning event, the system checks to see if there are any decommissioning events in the event sequence earlier than the current decommissioning event. If there are earlier decommissioning events in the event sequence for the EPC, then the system sets the EPC state to a condition reflecting error as there should not be any events after a decommissioning event.

For each listed EPC that is for an individual item, the system checks for the existence of only one commissioning event earlier in the event sequence then the current event. If there is more than one commissioning event or no commissioning event, then the system sets the EPC state to a condition reflecting error as there should be one (and only one) commissioning event for an individual item.

For each listed EPC that is for a container that is not reusable, the system checks for the existence of only one commissioning event earlier in the event sequence then the current event. If there is more than one commissioning event or no commissioning event, then the system sets the EPC state to a condition reflecting error as there should be one (and only one) commissioning event for the container.

Handling Shipping Events

When the system receives a shipping event from an entity in the supply chain, the shipping event may be handled in the following manner by various embodiments. For each EPC listed within the shipping event, the system determines whether the EPC is known. If the EPC is not known, the system records the EPC and stores the EPC information in the repository. The system then associates the shipping event with the EPC, whether the EPC was previously known or not. In addition, the system will determine additional EPCs from any parent/child containment relationships in a recursive matter, and associate the shipping event with those additional EPCs as well.

For each EPC associated with the shipping event, the system determines whether an event sequence exists for the EPC. If an event sequence exists, the system may perform a preliminary assessment of the event sequence relative to this shipping event as follows. If an event sequence does not exist, the system initiates an event sequence for the EPC with the shipping event as the initial event for the EPC. If the EPC is for an item and the event sequence does not exist, then the system sets the EPC state to note a missing commissioning event condition. If the EPC is for a container and the event sequence does not exist, then the system sets the EPC state to note a missing aggregation event condition.

In accordance with various embodiments, the preliminary assessment of each EPC event sequence may include:

If a decommissioning event exists earlier in the event sequence, then the system sets the EPC state to a condition reflecting error as there should not be any events after a decommissioning event.

If the EPC is for an individual item, then the system checks for existence of only one commissioning event earlier in the event sequence then the current event. If there is more than one commissioning event or no commissioning event, then the system sets the EPC state to a condition reflecting error as there should be one (and only one) commissioning event for an individual item.

If the EPC is for a container that is not reusable, then the system should check that there is only one commissioning event earlier in the event sequence than the current event. If there is more than one commissioning event, then the system sets the EPC state to a condition reflecting error as there should only be one commissioning event.

If the EPC is for a container that is not reusable, then the system should check for any disaggregation events earlier in the event sequence than the current aggregation event. If a disaggregation event exists and the EPC appears as parent in the earlier disaggregation event, then the system sets the EPC state to a condition reflecting error as an open container cannot be shipped.

If the EPC is for a container that is not reusable, then the system should check for the existence of at least one aggregation event where the EPC appears as parent that occurs earlier in the event sequence than the current aggregation event. If such an aggregation event does not exist, then the system sets the EPC state to a condition reflecting error as non-reusable containers should be parents before being shipped.

If the EPC is for a container and is reusable (e.g., tote), then the system should check that there is at least one aggregation event in which the EPC appears as parent earlier in the event sequence than the current event, but later than any receiving event, or there should exist at least one disaggregation event in which the EPC appears as parent earlier in the event sequence than the current event, but later than any receiving event. If neither such aggregation or disaggregation event exists, then the system sets the EPC state to a condition reflecting error as a reusable container is either a parent or is returning empty.

Handling Receiving Events

When the system receives a receiving event from an entity in the supply chain, the receiving event may be handled in the following manner by various embodiments. For each EPC listed within the receiving event, the system determines whether the EPC is known. If the EPC is not known, the system records the EPC and stores the EPC information in the repository. The system then associates the receiving event with the EPC, whether the EPC was previously known or not. In addition, the system will determine additional EPCs from any parent/child containment relationships in a recursive matter, and associate the receiving event with those additional EPCs as well.

For each EPC associated with the receiving event, the system determines whether an event sequence exists for the EPC. If an event sequence exists, the system may perform a preliminary assessment of the event sequence relative to this receiving event as follows. If an event sequence does not exist, the system initiates an event sequence for the EPC with the receiving event as the initial event for the EPC. If the EPC is for an item and the event sequence does not exist, then the system sets the EPC state to note a missing commissioning event condition. If the EPC is for a container and the event sequence does not exist, then the system sets the EPC state to note a missing aggregation event condition.

In accordance with various embodiments, the preliminary assessment of each EPC event sequence may include:

If a decommissioning event exists earlier in the event sequence, then the system sets the EPC state to a condition reflecting error as there should not be any events after a decommissioning event.

The system should check for the existence of a matching shipping event earlier in the event sequence than the current receiving event. If there is no matching shipping event, then the system sets the EPC state to a condition reflecting the error.

If the EPC is for an individual item, then the system checks for existence of only one commissioning event earlier in the event sequence then the current event. If there is more than one commissioning event or no commissioning event, then the system sets the EPC state to a condition reflecting error as there should be one (and only one) commissioning event for an individual item.

If the EPC is for a container that is not reusable, then the system should check that there is only one commissioning event earlier in the event sequence than the current event. If there is more than one commissioning event, then the system sets the EPC state to a condition reflecting error as there should only be one commissioning event.

If the EPC is for a container that is not reusable, then the system should check for any disaggregation events earlier in the event sequence than the current aggregation event. If a disaggregation event exists and the EPC appears as parent in the earlier disaggregation event, then the system sets the EPC state to a condition reflecting error as a previously open container cannot be received.

If the EPC is for a container that is not reusable, then the system should check for the existence of at least one aggregation event where the EPC appears as parent that occurs earlier in the event sequence than the current aggregation event. If such an aggregation event does not exist, then the system sets the EPC state to a condition reflecting error as non-reusable containers should be parents.

If the EPC is for a container and is reusable (e.g., tote), then the system should check that there is at least one aggregation event in which the EPC appears as parent earlier in the event sequence than the current event, but later than any receiving event, or there should exist at least one disaggregation event in which the EPC appears as parent earlier in the event sequence than the current event, but later than any receiving event. If neither such aggregation or disaggregation event exists, then the system sets the EPC state to a condition reflecting error as a reusable container is either a parent or is returning empty.

With reference to FIGS. 3-7, in the example shown, three partners (A, B, and C) are shown interacting. Trading Partner A (310) is a manufacturer who produces items for sale and publishes "commissioning" events 312, 313 to the external data repository server. In addition, Trading Partner A publishes "aggregation" events 314 describing the adding of units of sale into cases and "shipping" events 316 as Partner A ships its products to Trading Partner B (320), a distributor. Trading Partner A may maintain its own database which may contain events and other information internal to its operation and not published to the external data server.

Distributor 320 receives items produced by manufacturer 310 and retrieves events associated with the EPCs in the cases it received, as well as publishing "receiving" events 322 in response to receiving items. In addition, distributor 320 publishes shipping events 326, 328 to the external data repository server in response to reshipping the cases to Trading Partner C (330), a provider (e.g., a pharmacy). Distributor B (320) publishes disaggregation events 324 in response to removing units of sale from cases and shipping the units of sale to provider 330. Provider 330 receives items produced by manufacturer 310 and publishes "receiving" events 332, 334 in response to it receiving items.

Figure 4:
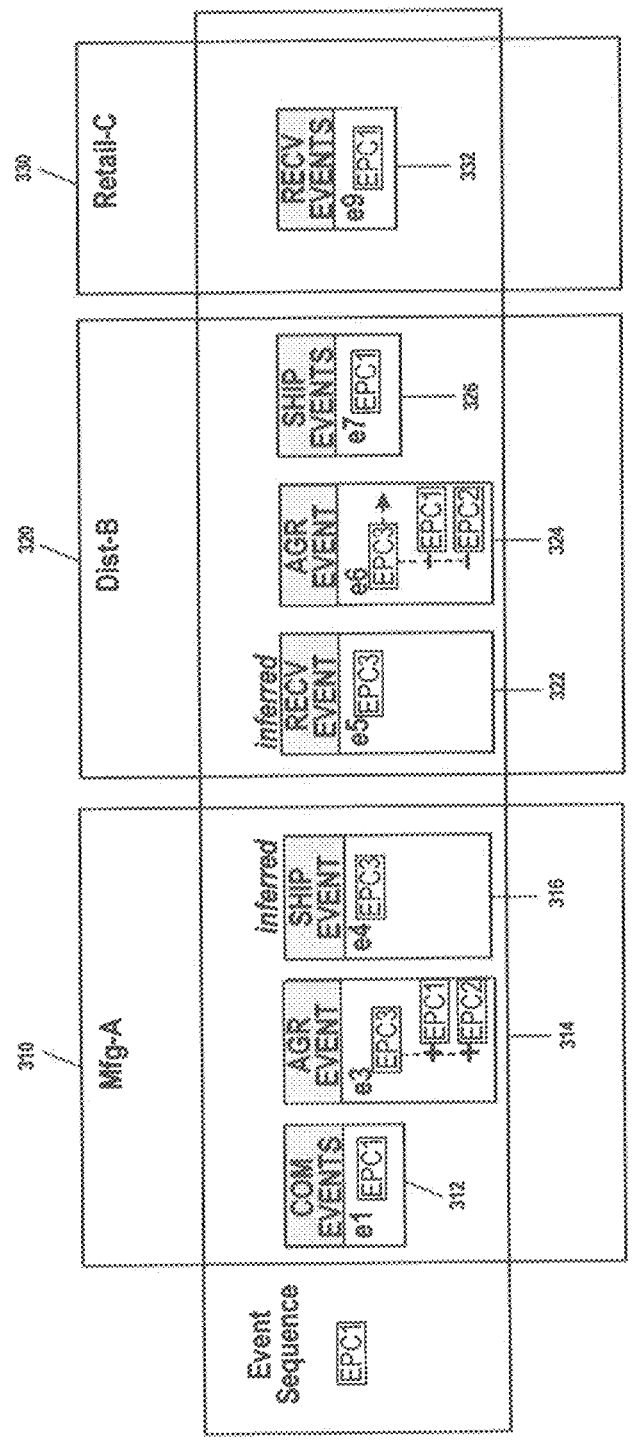
Figure 5:
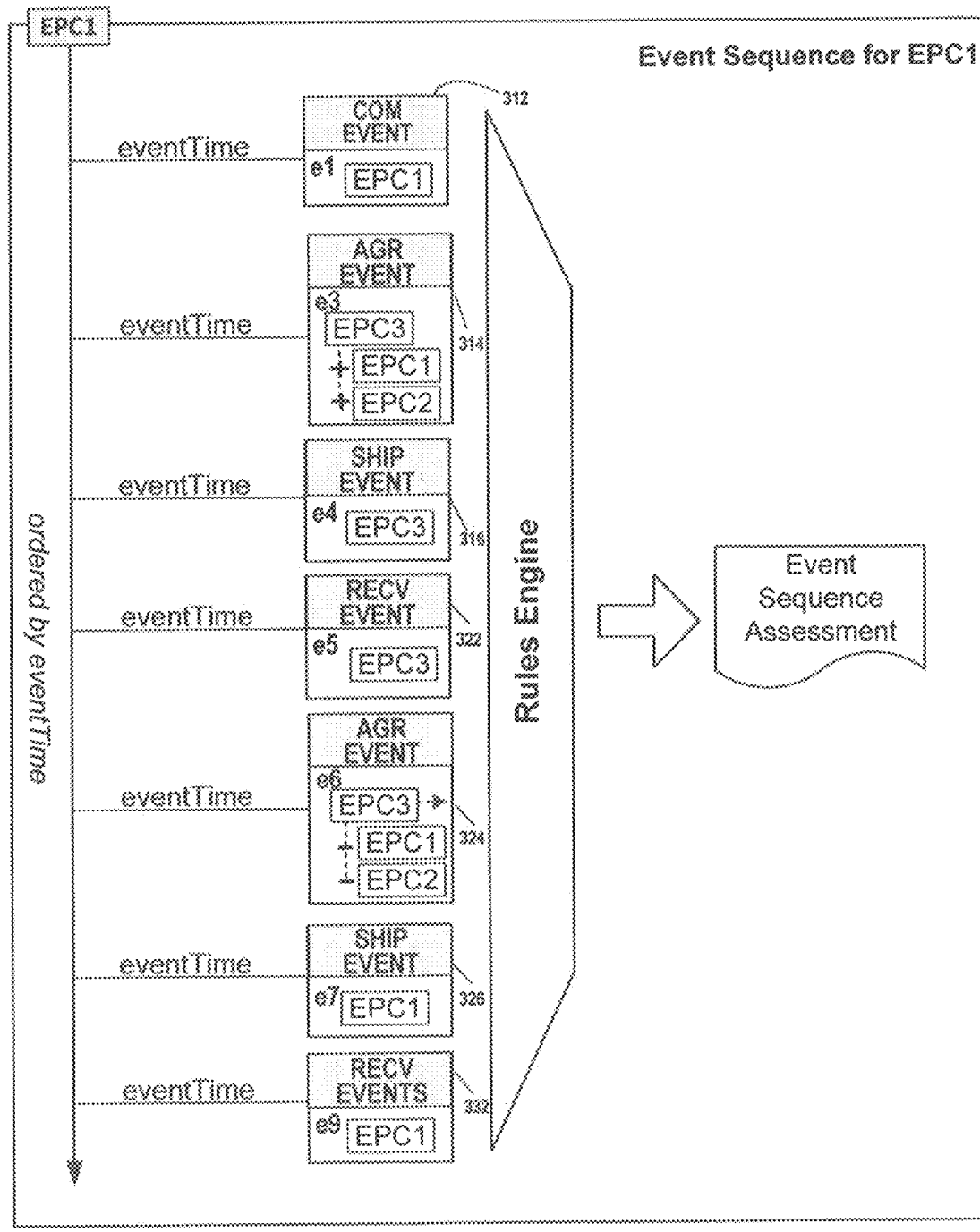
Figure 7:
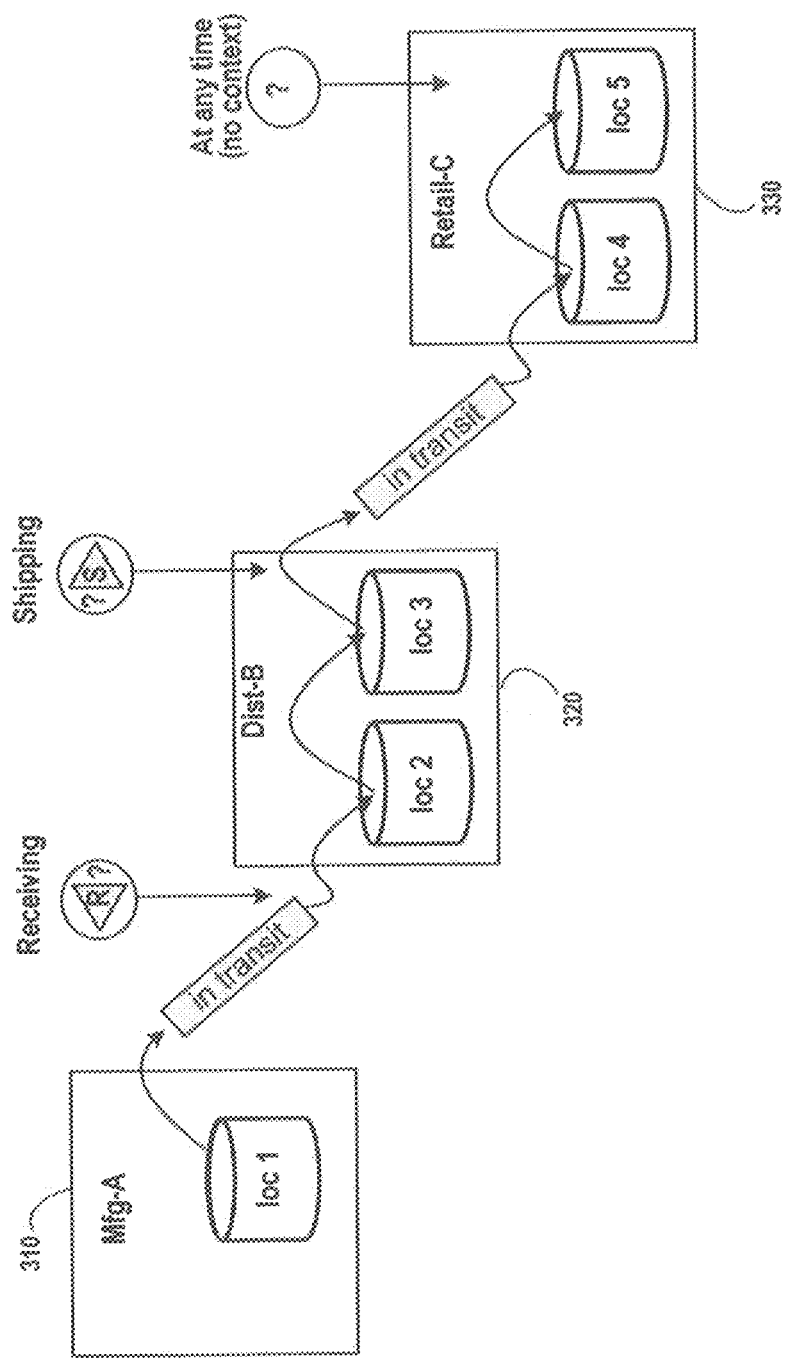

By logging and analyzing such events, various embodiments can quickly, accurately, and efficiently locate items in a supply chain. The system may also dynamically include or exclude inferred events in the event sequence associated with an EPC by traversing published (known) events for the EPC. For example, as shown in FIG. 4, shipping event 316 and receiving event 322 may be inferred by traversing the published events. Events relating to containers containing an individual item (at any level of nesting within other containers) may include events associated with the item until a disaggregation event involving the contained item occurs, at which point the events associated with the removed item can be removed from the container's event list.

Exemplary Process

The methods described below may be implemented in any manner, such as through a software program operating on a computer-based system. Such a software program may be stored on any computer-readable medium, such as floppy disks, hard disks, CD-ROMs, DVDs, any type of optical or magneto-optical disks, volatile or non-volatile memory, and/or any other type of media suitable for storing electronic instructions and capable of interfacing with a computing device. Methods according to embodiments of present disclosure may operate in conjunction with any type of computer system, such as a personal computer (PC), server, cellular phone, personal digital assistant (PDA), portable computer (such as a laptop), embedded computing system, and/or any other type of computing device. The computer system may include any number of computing devices connected in any manner, such as through a distributed network. The computer system may communicate and/or interface with any number of users and/or other computing devices to send and receive any suitable information in any manner, such as via a local area network (LAN), cellular communication, radio, satellite transmission, a modem, the Internet, and/or the like.

Figure 8:
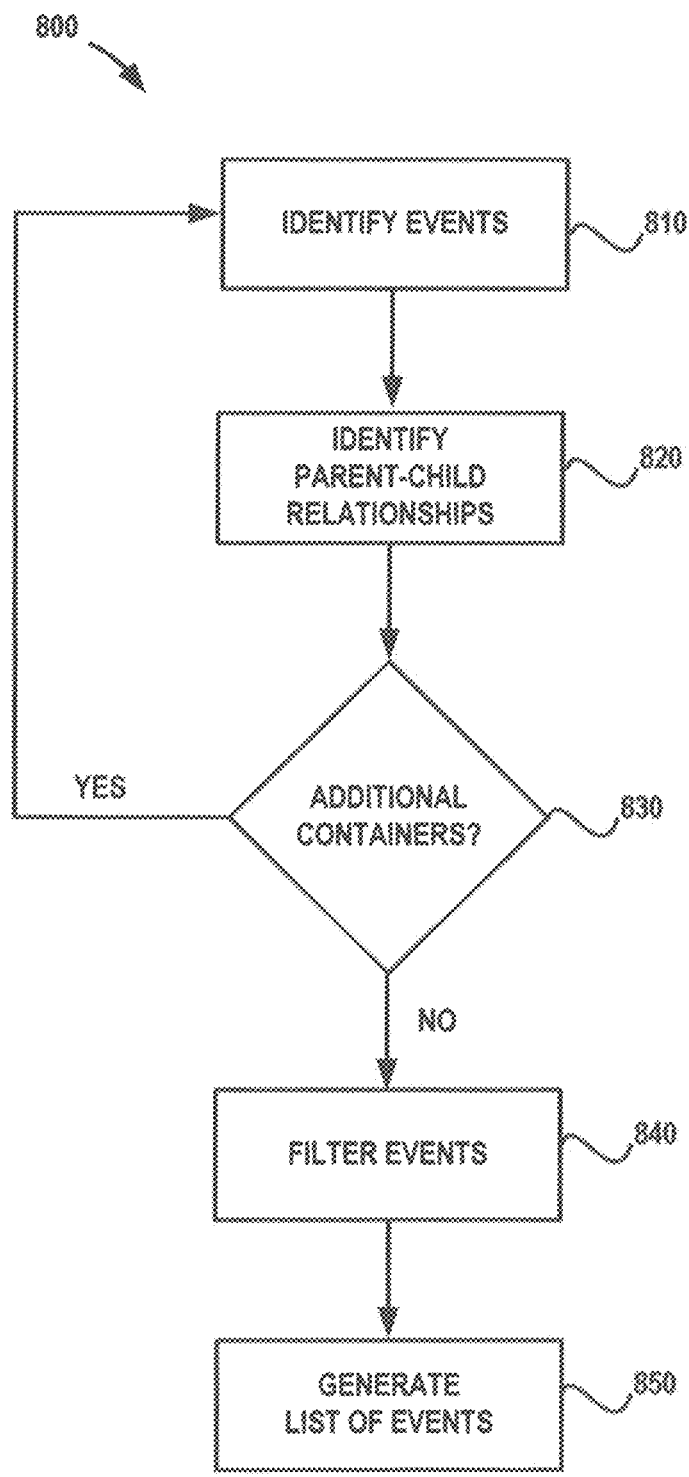
FIGS. 8-10 are flow diagrams illustrating exemplary processes, according to various embodiments.

FIG. 8 depicts an exemplary process 800 that may be utilized by various embodiments to generate an event sequence for a target item having an EPC:

1. For a target EPC, identify events directly associated with the EPC (810).
2. From those events, find containers that held the EPC using information from, for example, aggregation events to identify the parent-child relationships between the target item and the container(s) (820).
3. Repeat steps 1 & 2 on the container EPCs until no more events are found (830).
4. From this full set of events for all related EPCs, filter only those events that actually apply to the target EPC (840). So shipping and receiving events for a container may be classified as "in effect" between the aggregation and disaggregation events.
5. Generate a list of events (optionally sorted in time order), which captures everything that happened to the item identified by the target EPC (850).

The algorithm above (and variants thereof) can function despite events that are missing, duplicate events, or events that arrive out-of-order. Various embodiments may be configured to accept a set of target EPCs rather than just a single EPC and process them in batches to minimize database reads, thereby improving the efficiency of the process.

Various embodiments may be configured to handle any number of events arriving in any order and from multiple actors in a supply chain. For example, where a series of events associated with an EPC are published, but the events do not include an aggregation event, the event sequence can be automatically updated and properly reconciled in response to a party publishing the aggregation event.

The event sequence for an EPC may be constructed and assessed under a variety of different scenarios. Two such scenarios include a read (where a user or system requests some type of report) and a write (where a background process evaluates EPCs). The read may be provided on demand, while the write may be driven by the arrival of new events. Various embodiments may utilize a rules engine to apply the same rule set in both scenarios. In such cases, a user receives the latest information in response to requesting a report, and the background process allows alerts to be generated automatically. These results can also be cached to help improve efficiency.

Various embodiments are particularly effective in detecting counterfeit goods in a supply chain and preventing their distribution. For example, a counterfeiter could generate duplicate packaging and provide the fake product into a distributor's warehouse. The distributor may unknowingly ship both items (the real item and the counterfeit) to different destinations, generating valid EPCIS events for the shipments. Embodiments of this disclosure may receive both events, determine that two different event sequence chains exist for the same product, and generate an alert to the appropriate entities to, for example, halt further distribution of the shipments and/or to review the shipments to determine the source of the duplicate sequences.

While many conventional supply chain management systems enforce rigid constraints during the input process and reject events that might cause inconsistencies, various embodiments can provide a significantly more flexible solution to supply chain management by accepting events without such constraints and performing analyses to identify inconsistent events. In this manner, various embodiments may be better able to detect instances of broken inference, fraudulent packaging, and suspicious behavior compared to conventional systems.

Use of Rules Engine to Assess Event Sequence

In various embodiments, a rules engine is invoked on the events of an event sequence to assess the collection of the contained events. For example, various embodiments can determine whether there are missing events that "break the chain" of events tracing EPCs in the supply chain. Additionally, various embodiments can detect suspicious events that may indicate fraudulent handing or publishing of events.

Various embodiments may utilize a rules engine to add structure to the event set and perform conditional tests on that structure. Various embodiments may operate in conjunction with any desired rules in any format. For example, the following exemplary rules are defined in the Drools language for execution in that run-time rule engine, with software supplying the event structure and content. Various embodiments of the disclosure can also include helper functions or callbacks to the Drools rule engine. Various embodiments may utilize some, all, or different rules than those listed below. Rules may be stored in a database, text file, or any other suitable source for retrieval by the rules engine.

General Rules to Evaluate Known Conditions

No Commissioning Event—If an EPC does not have a commissioning event, then mark it as "inconsistent" and return an error.

Too Many Commissioning Events—If an EPC has more than one commissioning event, then mark it as "suspect" and return an error.

Receiving Event Without Shipping Event—If an EPC has a receiving event (R), look for a matching shipping event (S). The match occurs in response to the bizLocation identifier in R being owned by the same organization as the shipTo identifier in S. Note: this event allows for some leniency in the ownership structure. Large organizations may have acquired or divested companies. Customers may be free to define more strict rules that require an exact match. We can also apply regulatory rules based on state jurisdiction. If a match cannot be found, then mark this EPC as "inconsistent" and return an error.

Shipping Without Receiving Or Commissioning Event—If a user performs a Custody Check before shipping, a determination can be made as to whether they have a matching commissioning or receiving event for that EPC. The match occurs in response to the event's bizLocation being owned by the same organization that performs the check. If a match cannot be found, then mark this EPC as "inconsistent" and return an error.

Receiving Without Shipping Event—If a user performs a Custody Check before receiving, a determination can be made to identify a matching shipping event for that EPC. The match occurs in response to the event's shipTo identifier being owned by the same organization that performs the check. If a match cannot be found, then mark this EPC as "inconsistent" and return an error.

Expired Trigger—If an EPC has a commissioning event with an expiration date and today is beyond that date, then mark this EPC as "expired" and return an error.

Stolen Event—If any event has a disposition of "stolen," then mark this EPC as "stolen" and return an error.

Lost Event—If any event has a disposition of "lost," then mark this EPC as "lost" and return an error.

Recalled Event—If any event has a disposition of "recalled," then mark this EPC as "recalled" and return an error.

Context Location Not Owned By Requester—If a user performs a Custody Check using a location identifier owned by a different organization, then mark this EPC as "suspect" and return an error.

EPC In Two Places At Once—Events have bizLocation identifiers, which translate to known addresses. If any two events indicate that the product travelled faster than 500 mph between the locations, then mark the EPC as "suspect" and return an error.

Cold Chain Trigger—If any event contains physical measurement information (i.e., temperature) that violate the constraints defined for the product, then mark the EPC as "suspect" and return an error.

License Check—If any event contains license information, then check each license against the proper authority. If any license is not "in good standing" or "current," then mark the EPC as "suspect" and return an error.

Too Many Checks—If the number of requests exceeds a given threshold, then mark the EPC as "suspect" and return an error. This can be an indication of fraudulent activity.

Rules to Create New Links from Related Events

Commissioning Event Link To Shipping Event—If a commissioning event matches a shipping event, then create an EventLink for them. A match occurs in response to the events referencing the same EPC, they have bizLocation identifiers owned by the same organization, the commissioning event occurred before (or at the same time as) the shipping event, and an aggregation event has not occurred.

Shipping Event Link To Receiving Event—If a shipping event matches a receiving event, then create an EventLink for them. A match occurs in response to the events referencing the same EPC, the shipping event's shipTo identifier is owned by the same organization as the receiving event's bizLocation identifier, and the shipping event occurred before (or at the same time as) the receiving event.

Receiving Event Link To Shipping Event—If a receiving event matches a shipping event, then create an EventLink for them. A match occurs in response to the events referencing the same EPC, they have bizLocation identifiers owned by the same organization, and the receiving event occurred before (or at the same time as) the shipping event.

Child Commissioning Event Link To Aggregation Event—If a commissioning event matches an aggregation event, then create an EventLink for them. A match occurs when the aggregation event has a child EPC referenced in the commissioning event, they have bizLocation identifiers owned by the same organization, and the commissioning event occurred before (or at the same time as) the aggregation event.

Parent Commissioning Event Link To Aggregation Event—If a commissioning event matches an aggregation event, then create an EventLink for them. A match occurs in response to the aggregation event having a parent EPC referenced in the commissioning event, they have bizLocation identifiers owned by the same organization, and the commissioning event occurred before (or at the same time as) the aggregation event.

Aggregation Event Link To Shipping Event—If an aggregation event matches a shipping event, then create an EventLink for them. A match occurs in response to the events having bizLocation identifiers owned by the same organization, and the aggregation event occurred before (or at the same time as) the shipping event.

Receiving Event Link To Disaggregation Event—If a receiving event matches a disaggregation event, then create an EventLink for them. A match occurs in response to the disaggregation event having a parent EPC referenced in the receiving event, the events have bizLocation identifiers owned by the same organization, and the receiving event occurred before (or at the same time as) the disaggregation event.

Disaggregation Event Link To Decommissioning Event—If a disaggregation event matches a decommissioning event, then create an EventLink for them. A match occurs when the disaggregation event has a child EPC referenced in the decommissioning event, the events have bizLocation identifiers owned by the same organization, and the disaggregation event occurred before (or at the same time as) the decommissioning event.

Aggregation Event Link To Disaggregation Event—If an aggregation event matches a disaggregation event, then create an EventLink for them. A match occurs in response to the events referencing the same child EPC, the events have bizLocation identifiers owned by the same organization, and the aggregation event occurred before (or at the same time as) the disaggregation event.

Disaggregation Event Link To Aggregation Event—If a disaggregation event matches an aggregation event, then create an EventLink for them. A match occurs in response to the events referencing the same child EPC, the events have bizLocation identifiers owned by the same organization, and the disaggregation event occurred before (or at the same time as) the aggregation event.

Disaggregation Event Link to Shipping Event—If a disaggregation event matches a shipping event, then create an EventLink for them. A match occurs in response to the disaggregation event having a child EPC referenced in the shipping event, the events have bizLocation identifiers owned by the same organization, and the disaggregation event occurred before (or at the same time as) the shipping event.

Rules to Identify Unlinked Events

Commissioning Event Not Link To Shipping Event Or Aggregation Event—If a commissioning event cannot be matched to a shipping or aggregation event, then mark it as unlinked.

Shipping Event Not Link To Commissioning Event Or Receiving Event—If a shipping event cannot be linked to a commissioning or receiving event, then mark it as unlinked.

Receiving Event Not Link To Shipping Event—If a receiving event cannot be linked to a shipping event, then mark it as unlinked.

Disaggregation Event Not Link To Receiving Event—If a disaggregation event cannot be linked to a receiving event, then mark it as unlinked.

Stolen Event Published—If an event has a disposition of "stolen," then mark it as unlinked.

Lost Event Published—If an event has a disposition of "lost," then mark it as unlinked.

Recalled Event Published—If an event has a disposition of "recalled," then mark it as unlinked.

Miscellaneous Rules

LinkLink—From the EventLinks published by all of the preceding rules, join them together into trees of LinkLinks. This rule is applied recursively until all possibilities have been considered. This rule can be run after previous rules are published and used to associate links into event chains.

RootLink—From all of the EventLinks and LinkLinks published by the preceding rules, identify the root links of the trees. These have the condition where no other links are connected to them. This rule can be run after previous rules to find the roots of all chains.

Rules may generate any of a variety of outputs after being applied, including, for example: an assessment of the event sequence state; a list of any errors, each with details describing the context; a list of events, containing both the linked and unlinked events; and a set of root links, each including a handle to an event chain.

In various embodiments, if the trading partners in a supply chain have supplied a perfect set of events, then there is only one root link. If data is missing, incorrect or corrupt, then the rules generate multiple root links. This bad condition impacts the total assessment for the event sequence. The rules described above cover various business practices within the supply chain. Parties may define their own rules to cover specific requirements. For instance, a pharmacy may require certain information from the manufacturer in the commissioning event. These rules can be applied to the commissioning event after a shipping event indicates that the pharmacy will receive the product.

According to various embodiments, parties may generate and test their own custom rules using an interactive web-based user interface. In various embodiments, rules can be generated using an if-condition-then-action format, with the conditions chosen from a drop-down list and the action limited to a set of common choices (error, mark, log, etc.). Parties in the supply chain may also generate rules in any other suitable manner. For example, such parties may parameterize both conditions and actions, and then save the rules to a persistent store. A party's custom rules may be selectively applied in response to the party participating in an event sequence.

Output from application of the rules can be handed in any suitable manner according to any desired criteria. For example, rules output may be handled differently depending on how the assessment was invoked: if it was performed as part of a real-time Custody Check, then the list of errors can be returned to the user; if a background process invoked the assessment, then the errors may trigger notification or alerts to subscribed parties.

Events and Subscribers

Parties in the supply chain may subscribe to different events. Some exemplary subscriptions include: if a new shipping event contains a shipTo identifier owned by the subscribing party's organization, then push all of the upstream events to that party's communication channel; warn the subscribing party about any EPC that was recalled after it was received by the subscribing party; warn the subscribing party about any EPC that has expired received by the subscriber but that has not shipped. As discussed in more detail below, events that can be viewed by various parties in the supply chain may be subject to visibility constraints.

Embodiments of the disclosure can help various members of a supply chain to check an item to see if it has an appropriate chain of custody. Other information can be made available to participants based on (for example) their agreements with their trading partners. For example, the status information may indicate the history of the item is complete, or that there has been an alert on the item. If the item has an alert, a user with sufficient access rights may, through a user interface, obtain more information from the data repository, such as the error or warning message. In this manner, various embodiments of the disclosure can provide such users with a quick, efficient visual verification of an item's status.

Various embodiments may allow events and information to be "pushed" to a party before the party receives the product associated with the events and information. This provides the receiving party with a "time window." Among other things, this helps ensure that events are cached as close to the receiving facility as possible, allows problems with the event content to be resolved, reduces or eliminate the need for real-time queries against remote databases, and allows the receiving party time to fix network or system outages.

By having a record of all the events, systems can notify parties of adverse conditions. For example, a party may subscribe to any event that indicates stolen or recalled EPCs. In various embodiments, a data repository server may be configured to push recall events to parties in the supply chain and, depending on the visibility rules in effect, list only the recalled EPCs handled by the receiving party, but not EPCs that were not handled by the party.

In various embodiments, an exemplary process for recall notification includes receiving, by the data repository server, a recall event for a set of EPCs. In response to the recall notification, the server identifies all of the parties who published events for the EPCs in the recall notification. Visibility constraints are applied to the event. For each party in the supply chain, a modified event is generated that includes the recalled EPCs for that party, and then provided to the party, allowing all parties who handled the recalled EPCs to quickly know if they have (or have handled) any recalled products.

Error Resolution

Exceptions may be triggered by a number of scenarios, and may be corrected in any suitable manner. For example, the party that published the event that resulted in an exception may publish a correcting transaction (such as a shipping transaction to return goods received in error) in addition to their normal exception handling process. Exceptions may include information describing the business condition of an item, such as "shipped," "received," "damaged," etc.

Various embodiments may be configured to issue alerts or notifications in response to detecting stolen or counterfeit products, and may generate any number and type of exceptions as desired. For example, exceptions may include:

Recall Events—situations where a manufacturer requires the return of goods or a product already shipped to market or sold to consumers but discovered to be defective, contaminated or unsafe.

Return Events—situations where the owner of a product returns the product back to the previous owner or a disposal entity/reverse distributor.

Unplanned Disaggregations—situations where items/containers become disassociated from their containers during transit, such as where a pallet of cases is broken apart in order to fit in an airplane cargo hold. The cases are no longer physically tied to the original pallet but the data is still aggregated in an Aggregation event.

Data Exceptions—including:

Scan Read Errors—tag/barcode damaged and unreadable; tag/barcode has invalid format;

Documentation serial discrepancy (different serial numbers, correct lot);

Documentation lot discrepancy (correct serial numbers, different lot);

Documentation serial and lot are incorrect;

Wrong address;

Customer information is incorrect or missing;

Product descriptive information is incorrect or missing;

Product shipment information (invoice number, license number and/or description) is incorrect or missing;

Chain of Custody data is missing (transaction, ASN, and/or paperwork not received) for all or part of shipment;

Data security mismatch—Chain of Custody data received, but security keys don't match and can't be read;

Chain of Custody data in invalid format;
Container identifier isn't in data;
Container identifier is in data, but children inside are not in data; and
Product shipped to wrong customer, Track and Trace data sent to correct customer.
Broken Chain of Custody—Data is missing from one or more previous touch points. For example, where a Manufacturer ships to a Wholesaler, and a Wholesaler ships to a Retailer, the Retailer reviews documentation and data doesn't include the information from the original shipment from Manufacturer to Wholesaler. In another example, one of the parties of the supply chain does not publish events to the repository.
Suspected counterfeit shipment.
Undelivered Shipment.
Overage—Receipt of more physical product than expected.
Product received from unidentified sender—Shipment arrives from sender that does not have valid sales order or purchase order.
Received product in error—Shipped product misdirected to wrong recipient (case intended for recipient A is received by recipient B).
Shortage—Receipt of physical product without appropriate event data or receipt of event data without matching physical product. A shortage can be for parts of a shipment or parts of a return shipment.
Damage—Part of shipment damaged in-transit.

In various embodiments, some error conditions can be resolved by a single party, while other cases may require coordinated activity across the supply chain. For example, resolution of an aggregation error discovered by a pharmacy may include the manufacturer and distributor. Likewise, an aggregation error for one container may affect another container, and therefore the problem may ripple through a different distributor. Systems and methods of this disclosure help facilitate communication among the various supply chain participants, as well as to initiate and coordinate activities directed to resolving errors. In various embodiments, metrics and statistics can be gathered and created to determine the level of effectiveness of various parties in resolving errors. This can help identify remedial training or other steps to help improve the overall quality of error resolution by the supply chain.

In various embodiments, a rules engine may be used to match immediate upstream with immediate downstream events into contiguous chains of events so that the position-dependent visibility constraints for each trading partner in a supply chain may be applied. For example, various embodiments may be configured such that events may be received and tracked in any order, but events received out of order (such as a shipping event before a commissioning event) may trigger an alert.

In various embodiments, some rules (such as those described above) can be used to organize events into links and chains. A rules engine may be used to perform an exhaustive search of all possible event combinations. In response to a rule joining two events into a Link, it inserts that Link back into the rules engine. Rules from the rules engine can then be used to organize the output of prior rules, thereby efficiently and effectively organizing EPCIS events. In various embodiments, this data structure is built by procedural logic rather than a rules engine.

Some events (such as recall, lost or stolen events) may occur out-of-order at any time, and may be recognized by the rules engine as unlinked to any other events. According to various embodiments, based on where a Trading Partner published some events in a chain, a determination is made as to the partner's visibility to all other events within that chain as follows: Within an event chain, the earliest and latest events published by the requesting partner are found; upstream events precede the earliest published event; and downstream events succeed the latest published event. In various embodiments, the "upstream events" are configured to apply before a Trading Partner published a receiving event. If their supplier published a shipping event where the "ShipTo" property identifies the Trading Partner, then that event can be treated as an "upstream event." Among other things, this lets the partner inspect the event history before accepting delivery of the product and to factor this information into their business practices.

Visibility Framework Applied to Event Sequences

In various embodiments, the rendered representation (e.g., via XML/XHTML/JSON etc.) of the event may be controlled as a function of the observing party's role and privileges in relation to events within an event sequence. For example, a Trading Partner may be granted full visibility of events they publish, limited visibility of events upstream from them in the Event Sequence, and full visibility of receiving events of other immediately downstream entities that the Trading Partner shipped to (also known as "one down events"). The Trading Partner may be restricted, however, from viewing events beyond the receiving event of the entities immediately downstream from the Trading Partner (also known as "greater than one down events").

Various embodiments may operate in conjunction with any number and type of visibility constraints, including restrictions on events that can be seen or not seen. For example, the local attribute of a "greater than one down" event may be raised in granularity to the state level which gives the upstream trading partner state level visibility of where goods are handled but not specifically the handling party. Visibility rules may also be applied to multiple event chains within the request context. This can happen under failure conditions like missing events, duplicate packaging, or fraud.

The following exemplary definitions may be used to describe aspects of a trading partner's visibility with regards to events in an event sequence:

Visibility Subject—anything that the trading partner may see, including event properties, events positioned within an event sequence, Custody Check actions and their properties, assessment results, etc.

Visibility Constraint—a level of granularity applied to a Visibility Subject. Examples are transparent, partially obscured, or hidden.

Visibility Specification—an association of Visibility Subjects to Visibility Constraints. This type parameterizes a filter to be applied to any thing that may be viewed.

Visibility Contract—aptures the business logic of "who can see what and when". The event publisher may also define Visibility Contracts to control how other parties view data. Event types may be determined by their order and relationship to the observe (e.g., upstream<published<one-down<greater-than-one-down)

Figure 9:
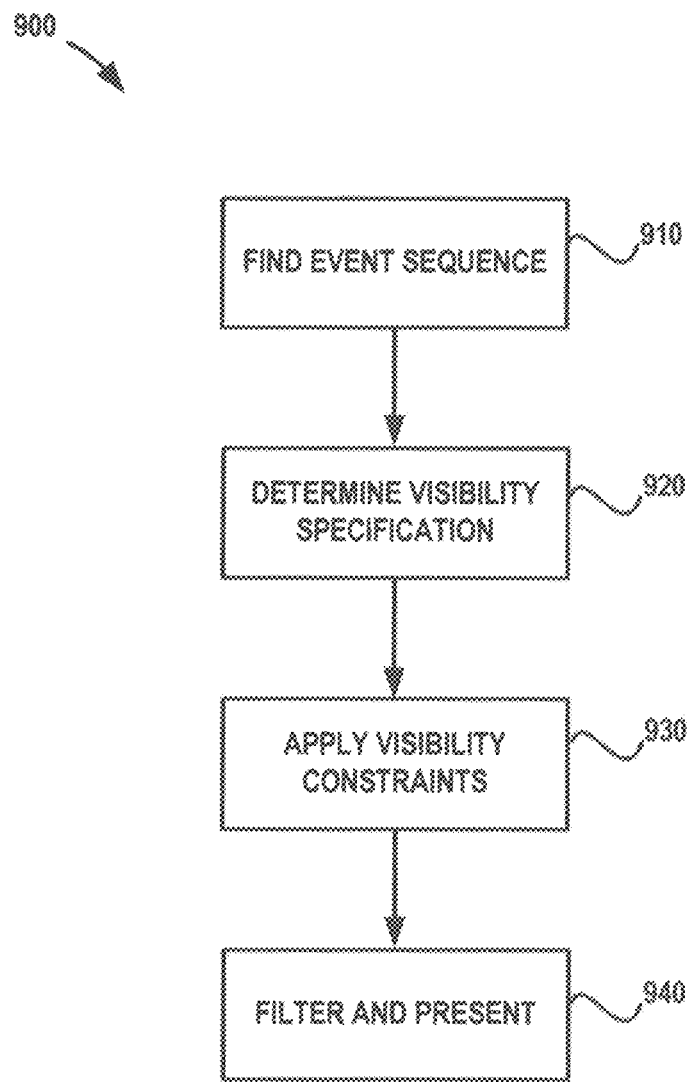

Given the previous definitions of upstream and downstream events, FIG. 9 depicts an exemplary process 900 that various embodiments may execute before rendering events to an observer. As shown in FIG. 9, exemplary method 900 includes:

1. Find the Event Sequence according to the previous discussion (910).

2. Determine the Visibility Specification from the highest priority source (920):
   A. The observer's company policy or role
   B. The observer's policy or role
   C. The Trading Partner who published each event
   D. The system-wide default
3. Apply the Visibility Constraints to all Subjects according to the Specifications (930).
4. Filter out any empty results and present to the observer (940).

Visibility Contracts

A Trading Partner may grant expanded visibility of its published events to other partners that the other partners would not otherwise have visibility to. This can be achieved by the publishing Trading Partner creating a contract between itself and another partner. This contract may have a date effective range associated with it.

In various embodiments, Trading Partners in a supply chain may upload Visibility Contracts to the external data repository server. The visibility contracts may be in any format (such as application-specific XML, format) and have any properties, such as the publisher of the contract, the associated events, the consumer of data (also called the "observer"), the effective start and end dates of the contract, and/or the Visibility Specification that applies in response to the consumer viewing publisher's events.

Systems and methods of the present disclosure may apply visibility constraints to some or all events. Any events pushed to a subscribed party can be so filtered. Various embodiments may also transform the pushed events to solve incompatibilities in the supply chain.

In various embodiments, for example, a pharmacy trading partner may require product data (dosage, active ingredients, drug name) within the commissioning events. However the manufacturer may publish such data to a separate repository (i.e., GSDN) rather than supply it via commissioning events. In such cases, the central data repository server may be configured to retrieve the product data needed by the pharmacy and augment any commissioning events with this information viewed by the pharmacy. This not only provides the pharmacy with the information it needs, but solves the problem without requiring the manufacturer to alter its process.

Systems and methods of the present disclosure may also be configured to help bridge evolving data processing or business transaction standards, namely by translating between different versions of a standard used by different parties within the same supply chain. Various embodiments may also be configured to normalize or format in different ways for different members of a supply chain. For example, a pharmacy may want all values of the national drug code (NDC) to be in a specific format.

Figure 10:
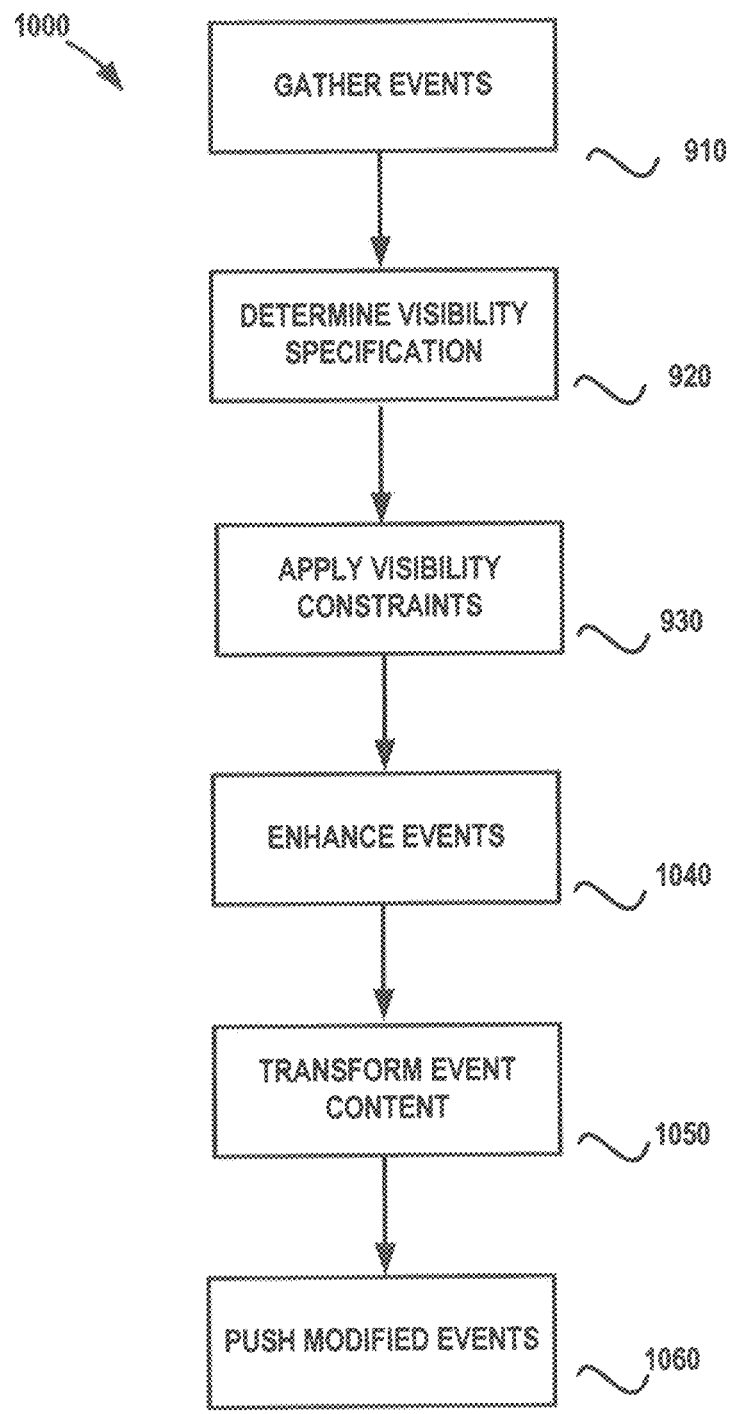

FIG. 10 depicts an exemplary process 1000 that various embodiments may implement that combine various visibility, transformation, and push features. As shown in FIG. 10, exemplary process 1000 includes:
1. When a shipping event contains a shipTo identifier for a receiving party, gather all upstream events (910).
2. Determine the Visibility Specification from the highest priority source (920) as described above.
2. Apply visibility constraints to the events, based on the default and publishers' policies (1030).
3. Enhance the events with data from other sources, based on the receiving party's policies (1040).
4. Transform event content, based on the receiving party's policies (1050).
5. Push the modified events to the receiving party via a communication channel (1060).

In accordance with various embodiments, FIGS. 11-21 include exemplary screenshots associated with a hypothetical sequence of events associated with items produced by manufacturer 310 and shipped to distributor 320, then shipped from distributor 320 to pharmacy 330. In this example, the visibility constraints for this supply chain ensures that: Pharmacy 330 can see all of the locations where the events took place; Distributor 320 can see that a disaggregation event took place, but not where the event occurred; and Manufacturer 310 cannot see any locations beyond the Distributor's receiving event.

FIG. 11 illustrates the event sequence (also referred to as the "chain of custody") for a particular pharmaceutical item from the perspective of manufacturer 310. FIG. 12 illustrates the chain of custody from the perspective of distributor 320, while FIG. 13 illustrates the distributor's view of the events published by manufacturer 310 and FIG. 14 illustrates the distributor's view of its own events. FIG. 15 illustrates the chain of custody from the perspective of pharmacy 330. FIG. 16 illustrates the events published by pharmacy 330 (as viewed by the pharmacy), while FIG. 17 illustrates the events published by manufacturer 310 and distributor 320 from the perspective of pharmacy 330.

The chain of custody shows that Manufacturer 310 packaged 2 items within shipping container #440 (see aggregation event in FIG. 13), and Distributor 320 received and opened the container (see receiving and disaggregation events in FIG. 14). A few days later the Items were packaged into a different shipping container (#297—see aggregation event in FIG. 14), then shipped to Pharmacy 330. Pharmacy 330 received the container, then later removed the Items (receiving and disaggregation events in FIG. 16). As shown in FIG. 14, Distributor 320 performed a container Custody Check before shipping to Pharmacy 330. Among other things, this helps ensure that all items within the container are still in a consistent state (i.e.—no recalls, counterfeits, etc.). Also shown from the screenshots, the Distributor can see only the date and time of Disaggregation, not the event details.

From the Pharmacy's perspective, the chain of custody shows that Manufacturer 310 packaged 2 items within shipping container #994; Distributor 320 received and shipped the container as-is, unopened, and Pharmacy 330 performed a Custody Check before receiving the container. The chain of custody returned "good," and Pharmacy 330 accepted the container then opened it a few days later. In this example, it can be seen that Items in the Pharmacy's Disaggregation event match the Manufacturer's Aggregation event.

FIG. 18 illustrates a lot report requested by manufacturer 310 prior to issuing a recall. In this example, the manufacturer's view of the locations of the items is limited to the state they are in. FIG. 19 illustrates the distributor's view of the chain of custody after manufacturer 310 issued a recall for the item. In this example, Distributor 320 performed one Custody Check before receiving, then another before shipping the product to Pharmacy 330. This second check detects that Manufacturer 310 published a "holding" event. Distributor 320 interrupts the normal shipping procedure because of this recalled state. FIG. 20 illustrates the chain of custody for the item after a recall is issued by the manufacturer from the Distributor's perspective, and FIG. 21 the Distributor's view of the holding event.

Various embodiments can track product containers or packages uniquely serialized or identified at the lowest sellable unit level (smallest package or immediate container) and can be used by any number of entities, including manufacturers, wholesalers, and pharmacies (providers) in a supply chain. Various embodiments also allow interaction with other systems, including proprietary systems used by different trading partners in a supply chain. In various embodiments, communication with such entities is performed via an application programming interface (API) supported by the external data repository to allow communication between the repository and the various trading partners in the supply chain.

Various embodiments may secure data stored in the repository (such as track and trace data and other data used to facilitate chain of custody tracking) in any suitable manner, including various forms of encryption. Various embodiments may also redact data provided to members of a supply chain to, for example, maintain the confidentiality of a patient using a healthcare product.

Reporting

Various embodiments may receive, gather, and analyze metrics regarding events in a supply chain, and may provide such metrics and other information to users via various reports. Such reports may include information about products and their availability in the supply chain as well as custody chains for individual items or groups of items or containers. Reports can be provided in any suitable manner, such as via a web user interface or via an electronic communication.

The following is a non-exclusive, exemplary list of data that may be provided in a report provided by various embodiments:

Event Information: Event/Transaction Identifier; Item/Container Identifier; Event Timestamp; Event Type; Event Location(s); Event Party/Parties; Event Business Step; Event Disposition; Event Action; Sales Invoice Number or customer-specific shipping reference number linked to invoice; Number of Containers in event.

Product Information: NDC; Batch/Lot Number and Expiration Date (from the commissioning event); Trade or generic name of drug; Quantity of Drug; Dosage Form; Strength; Container Size.

Party Information: Manufacturer Name; Federal Manufacturer's Registration Number (or state license number); Name of each person certifying delivery/receipt of drug.

Location Information: Principal address of the Manufacturer; Address of each person certifying delivery/receipt of drug.

The detailed description of various embodiments herein makes reference to the accompanying figures, which show the exemplary embodiments by way of illustration. While these exemplary embodiments are described in sufficient detail to enable those skilled in the art to practice the disclosure, it should be understood that other embodiments may be realized and that logical and mechanical changes may be made without departing from the spirit and scope of the disclosure. Thus, the detailed description herein is presented for purposes of illustration only and not of limitation. For example, the steps recited in any of the method or process descriptions may be executed in any order and are not limited to the order presented. Moreover, any of the functions or steps may be outsourced to or performed by one or more third parties. Furthermore, any reference to singular includes plural embodiments, and any reference to more than one component may include a singular embodiment. Definitions for terms that may be used throughout this disclosure are exemplary and non-exclusive. The terms used in this disclosure may have alternate meanings or definitions consistent with the disclosure, and the present disclosure is not limited to any particular definition or interpretation of any particular term.

Systems, methods and computer program products are provided. In the detailed description herein, references to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Any communication, transmission and/or channel discussed herein may include any system or method for delivering content (e.g., data, information, metadata, etc.), and/or the content itself. The content may be presented in any form or medium, and in various embodiments, the content may be delivered electronically and/or capable of being presented electronically.

In various embodiments, the methods described herein are implemented using the various particular machines described herein. The methods described herein may be implemented using the below particular machines, and those hereinafter developed, in any suitable combination, as would be appreciated immediately by one skilled in the art. Further, as is unambiguous from this disclosure, the methods described herein may result in various transformations of certain articles.

For the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: client data; merchant data; financial institution data; and/or like data useful in the operation of the system. As those skilled in the art will appreciate, user computer may include an operating system (e.g., Windows NT, Windows 95/98/2000, Windows XP, Windows Vista, Windows 7, OS2, UNIX, Linux, Solaris, MacOS, etc.) as well as various conventional support software and drivers typically associated with computers.

The present system or any part(s) or function(s) thereof may be implemented using hardware, software or a combination thereof and may be implemented in one or more computer systems or other processing systems. However, the manipulations performed by embodiments were often referred to in terms, such as matching or selecting, which are commonly associated with mental operations performed by a human operator. No such capability of a human operator is necessary, or desirable in most cases, in any of the operations described herein. Rather, the operations may be machine operations. Useful machines for performing the various embodiments include general purpose digital computers or similar devices.

Various embodiments may be directed toward one or more computer systems capable of carrying out the functionality described herein. The computer system may include one or more processors connected to a communication infrastructure (e.g., a communications bus, cross over bar, or network). Such computer systems can also include a display interface that forwards graphics, text, and other data from the communication infrastructure (or from a frame buffer not shown) for display on a display unit. Such computer systems may include one or more memories, such as a random-access memory (RAM), read-only memory (ROM), a hard disk drive and/or a removable storage drive, a floppy disk drive, a magnetic tape drive, and/or an optical disk drive. The removable storage drive reads from and/or writes to a removable storage unit in a well-known manner. Removable storage unit represents a floppy disk, magnetic tape, optical disk, etc. which is read by and written to by removable storage drive. As will be appreciated, the removable storage unit includes a computer usable storage medium having stored therein computer software and/or data.

In various embodiments, secondary memory may include other similar devices for allowing computer programs or other instructions to be loaded into computer system. Such devices may include, for example, a removable storage unit and an interface. Examples of such may include a program cartridge and cartridge interface (such as that found in video game devices), a removable memory chip (such as an erasable programmable read only memory (EPROM), or programmable read only memory (PROM)) and associated socket, and other removable storage units and interfaces, which allow software and data to be transferred from the removable storage unit to computer system.

Computer system may also include a communications interface. Communications interface allows software and data to be transferred between computer system and external devices. Examples of communications interface may include a modem, a network interface (such as an Ethernet card), a communications port, a Personal Computer Memory Card International Association (PCMCIA) slot and card, etc. Software and data transferred via communications interface are in the form of signals which may be electronic, electromagnetic, optical or other signals capable of being received by communications interface. These signals are provided to communications interface via a communications path (e.g., channel). This channel carries signals and may be implemented using wire, cable, fiber optics, a telephone line, a cellular link, a radio frequency (RF) link, wireless and other communications channels.

The terms "computer program medium" and "computer usable medium" and "computer readable medium" are used to generally refer to media such as removable storage drive and a hard disk installed in hard disk drive. These computer program products provide software to computer system.

Computer programs (also referred to as computer control logic) may be stored in a main memory and/or secondary memory. Computer programs may also be received via communications interface. Such computer programs, when executed, enable the computer system to perform the features as discussed herein. In particular, the computer programs, when executed, enable the processor to perform the features of various embodiments. Accordingly, such computer programs represent controllers of the computer system.

In various embodiments, software may be stored in a computer program product and loaded into computer system using removable storage drive, hard disk drive or communications interface. The control logic (software), when executed by the processor, causes the processor to perform the functions of various embodiments as described herein. In various embodiments, hardware components such as application specific integrated circuits (ASICs). Implementation of the hardware state machine so as to perform the functions described herein will be apparent to persons skilled in the relevant art(s).

In various embodiments, the server may include application servers (e.g., WEB SPHERE, WEB LOGIC, JBOSS). In various embodiments, the server may include web servers (e.g., APACHE, IIS, GWS, SUN JAVA SYSTEM WEB SERVER).

A web client includes any device (e.g., personal computer) which communicates via any network, for example such as those discussed herein. Such browser applications comprise Internet browsing software installed within a computing unit or a system to conduct online transactions and/or communications. These computing units or systems may take the form of a computer or set of computers, although other types of computing units or systems may be used, including laptops, notebooks, tablets, hand held computers, personal digital assistants, set-top boxes, workstations, computer-servers, main frame computers, mini-computers, PC servers, pervasive computers, network sets of computers, personal computers, such as iPads, iMACs, and MacBooks, kiosks, terminals, point of sale (POS) devices and/or terminals, televisions, or any other device capable of receiving data over a network. A web-client may run Microsoft Internet Explorer, Mozilla Firefox, Google Chrome, Apple Safari, or any other of the myriad software packages available for browsing the internet.

Practitioners will appreciate that a web client may or may not be in direct contact with an application server. For example, a web client may access the services of an application server through another server and/or hardware component, which may have a direct or indirect connection to an Internet server. For example, a web client may communicate with an application server via a load balancer. In an exemplary embodiment, access is through a network or the Internet through a commercially-available web-browser software package.

As those skilled in the art will appreciate, a web client includes an operating system (e.g., Windows NT, 95/98/2000/CE/Mobile, OS2, UNIX, Linux, Solaris, MacOS, PalmOS, etc.) as well as various conventional support software and drivers typically associated with computers. A web client may include any suitable personal computer, network computer, workstation, personal digital assistant, cellular phone, smart phone, minicomputer, mainframe or the like. A web client can be in a home or business environment with access to a network. In an exemplary embodiment, access is through a network or the Internet through a commercially available web-browser software package. A web client may implement security protocols such as Secure Sockets Layer (SSL) and Transport Layer Security (TLS). A web client may implement several application layer protocols including http, https, ftp, and sftp.

In various embodiments, components, modules, and/or engines of system 100 may be implemented as micro-applications or micro-apps. Micro-apps are typically deployed in the context of a mobile operating system, including for example, a Palm mobile operating system, a Windows mobile operating system, an Android Operating System, Apple iOS, a Blackberry operating system and the like. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

As used herein, the term "network" includes any cloud, cloud computing system or electronic communications system or method which incorporates hardware and/or software components. Communication among the parties may be accomplished through any suitable communication channels, such as, for example, a telephone network, an extranet, an intranet, Internet, point of interaction device (point of sale device, personal digital assistant (e.g., iPhone®, Palm Pilot®, Blackberry®), cellular phone, kiosk, etc.), online communications, satellite communications, off-line communications, wireless communications, transponder communications, local area network (LAN), wide area network (WAN), virtual private network (VPN), networked or linked devices, keyboard, mouse and/or any suitable communication or data input modality. Moreover, although the system is frequently described herein as being implemented with TCP/IP communications protocols, the system may also be implemented using IPX, Appletalk, IP-6, NetBIOS, OSI, any tunneling protocol (e.g., IPsec, SSH), or any number of existing or future protocols. If the network is in the nature of a public network, such as the Internet, it may be advantageous to presume the network to be insecure and open to eavesdroppers. Specific information related to the protocols, standards, and application software utilized in connection with the Internet is generally known to those skilled in the art and, as such, need not be detailed herein. See, for example, DILIP NAIK, INTERNET STANDARDS AND PROTOCOLS (1998); JAVA 2 COMPLETE, various authors, (Sybex 1999); DEBORAH RAY AND ERIC RAY, MASTERING HTML 4.0 (1997); and LOSHIN, TCP/IP CLEARLY EXPLAINED (1997) and DAVID GOURLEY AND BRIAN TOTTY, HTTP, THE DEFINITIVE GUIDE (2002), the contents of which are hereby incorporated by reference.

The various system components may be independently, separately or collectively suitably coupled to the network via data links which includes, for example, a connection to an Internet Service Provider (ISP) over the local loop as is typically used in connection with standard modem communication, cable modem, Dish networks, ISDN, Digital Subscriber Line (DSL), or various wireless communication methods, see, e.g., GILBERT HELD, UNDERSTANDING DATA COMMUNICATIONS (1996), which is hereby incorporated by reference. It is noted that the network may be implemented as other types of networks, such as an interactive television (ITV) network. Moreover, the system contemplates the use, sale or distribution of any goods, services or information over any network having similar functionality described herein.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand. For more information regarding cloud computing, see the NIST's (National Institute of Standards and Technology) definition of cloud computing at http://csrc.nist.gov/publications/nistpubs/800-145/SP800-145.pdf (last visited June 2012), which is hereby incorporated by reference in its entirety.

As used herein, "transmit" may include sending electronic data from one system component to another over a network connection. Additionally, as used herein, "data" may include encompassing information such as commands, queries, files, data for storage, and the like in digital or any other form.

The system contemplates uses in association with web services, utility computing, pervasive and individualized computing, security and identity solutions, autonomic computing, cloud computing, commodity computing, mobility and wireless solutions, open source, biometrics, grid computing and/or mesh computing.

Any databases discussed herein may include relational, hierarchical, graphical, or object-oriented structure and/or any other database configurations. Common database products that may be used to implement the databases include DB2 by IBM (Armonk, NY), various database products available from Oracle Corporation (Redwood Shores, CA), Microsoft Access or Microsoft SQL Server by Microsoft Corporation (Redmond, Washington), MySQL by MySQL AB (Uppsala, Sweden), or any other suitable database product. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. In accordance with one embodiment, any suitable data storage technique may be utilized to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed via one or more keys, numeric, alphabetical by first tuple, etc.); Binary Large Object (BLOB); stored as ungrouped data elements encoded using ISO/IEC 7816-6 data elements; stored as ungrouped data elements encoded using ISO/IEC Abstract Syntax Notation (ASN.1) as in ISO/IEC 8824 and 8825; and/or other proprietary techniques that may include fractal compression methods, image compression methods, etc.

One skilled in the art will also appreciate that, for security reasons, any databases, systems, devices, servers or other components of the system may consist of any combination thereof at a single location or at multiple locations, wherein each database or system includes any of various suitable security features, such as firewalls, access codes, encryption, decryption, compression, decompression, and/or the like.

Encryption may be performed by way of any of the techniques now available in the art or which may become available—e.g., Twofish, RSA, El Gamal, Schorr signature, DSA, PGP, PKI, GPG (GnuPG), and symmetric and asymmetric cryptosystems.

The computing unit of the web client may be further equipped with an Internet browser connected to the Internet or an intranet using standard dial-up, cable, DSL or any other Internet protocol known in the art. Transactions originating at a web client may pass through a firewall in order to prevent unauthorized access from users of other networks. Further, additional firewalls may be deployed between the varying components of CMS to further enhance security.

Firewall may include any hardware and/or software suitably configured to protect CMS components and/or enterprise computing resources from users of other networks. Further, a firewall may be configured to limit or restrict access to various systems and components behind the firewall for web clients connecting through a web server. Firewall may reside in varying configurations including Stateful Inspection, Proxy based, access control lists, and Packet Filtering among others. Firewall may be integrated within an web server or any other CMS components or may further reside as a separate entity. A firewall may implement network address translation ("NAT") and/or network address port translation ("NAPT"). A firewall may accommodate various tunneling protocols to facilitate secure communications, such as those used in virtual private networking. A firewall may implement a demilitarized zone ("DMZ") to facilitate communications with a public network such as the Internet. A firewall may be integrated as software within an Internet server, any other application server components or may reside within another computing device or may take the form of a standalone hardware component.

The computers discussed herein may provide a suitable website or other Internet-based graphical user interface which is accessible by users. In one embodiment, the Microsoft Internet Information Server (IIS), Microsoft Transaction Server (MTS), and Microsoft SQL Server, are used in conjunction with the Microsoft operating system, Microsoft NT web server software, a Microsoft SQL Server database system, and a Microsoft Commerce Server. Additionally, components such as Access or Microsoft SQL Server, Oracle, Sybase, Informix MySQL, Interbase, etc., may be used to provide an Active Data Object (ADO) compliant database management system. In one embodiment, the Apache web server is used in conjunction with a Linux operating system, a MySQL database, and the Perl, PHP, and/or Python programming languages.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, Java applets, JavaScript, active server pages (ASP), common gateway interface scripts (CGI), extensible markup language (XML), dynamic HTML, cascading style sheets (CSS), AJAX (Asynchronous Javascript And XML), helper applications, plug-ins, and the like. A server may include a web service that receives a request from a web server, the request including a URL (http://yahoo.com/stockquotes/ge) and an IP address (123.56.789.234). The web server retrieves the appropriate web pages and sends the data or applications for the web pages to the IP address. Web services are applications that are capable of interacting with other applications over a communications means, such as the internet. Web services are typically based on standards or protocols such as XML, SOAP, AJAX, WSDL and UDDI. Web services methods are well known in the art, and are covered in many standard texts. See, e.g., ALEX NGHIEM, IT WEB SERVICES: A ROADMAP FOR THE ENTERPRISE (2003), hereby incorporated by reference.

Middleware may include any hardware and/or software suitably configured to facilitate communications and/or process transactions between disparate computing systems. Middleware components are commercially available and known in the art. Middleware may be implemented through commercially available hardware and/or software, through custom hardware and/or software components, or through a combination thereof. Middleware may reside in a variety of configurations and may exist as a standalone system or may be a software component residing on the Internet server. Middleware may be configured to process transactions between the various components of an application server and any number of internal or external systems for any of the purposes disclosed herein. WebSphere MQTM (formerly MQSeries) by IBM, Inc. (Armonk, NY) is an example of a commercially available middleware product. An Enterprise Service Bus ("ESB") application is another example of middleware.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

The system and method may be described herein in terms of functional block components, screen shots, optional selections and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C#, Java, JavaScript, VB Script, Macromedia Cold Fusion, COBOL, Microsoft Active Server Pages, assembly, PERL, PHP, awk, Python, Visual Basic, SQL Stored Procedures, PL/SQL, any UNIX shell script, and extensible markup language (XML) with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JavaScript, VBScript or the like. For a basic introduction of cryptography and network security, see any of the following references: (1) "Applied Cryptography: Protocols, Algorithms, And Source Code In C," by Bruce Schneier, published by John Wiley & Sons (second edition, 1995); (2) "Java Cryptography" by Jonathan Knudson, published by O'Reilly & Associates (1998); (3) "Cryptography & Network Security: Principles & Practice" by William Stallings, published by Prentice Hall; all of which are hereby incorporated by reference.

As will be appreciated by one of ordinary skill in the art, the system may be embodied as a customization of an existing system, an add-on product, a processing apparatus executing upgraded software, a stand-alone system, a distributed system, a method, a data processing system, a device for data processing, and/or a computer program product. Accordingly, any portion of the system or a module may take the form of a processing apparatus executing code, an internet based embodiment, an entirely hardware embodiment, or an embodiment combining aspects of the internet, software and hardware. Furthermore, the system may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

The systems and methods are described herein with reference to screen shots, block diagrams and flowchart illustrations of methods, apparatus (e.g., systems), and computer program products according to various embodiments. It will be understood that each functional block of the block diagrams and the flowchart illustrations, and combinations of functional blocks in the block diagrams and flowchart illustrations, respectively, can be implemented by computer program instructions.

Computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user windows, webpages, websites, web forms, prompts, etc. Practitioners will appreciate that the illustrated steps described herein may comprise in any number of configurations including the use of windows, webpages, web forms, popup windows, prompts and the like. It should be further appreciated that the multiple steps as illustrated and described may be combined into single webpages and/or windows but have been expanded for the sake of simplicity. In other cases, steps illustrated and described as single process steps may be separated into multiple webpages and/or windows but have been combined for simplicity.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Although the disclosure includes a method, it is contemplated that it may be embodied as computer program instructions on a tangible computer-readable carrier, such as a magnetic or optical memory or a magnetic or optical disk. All structural, chemical, and functional equivalents to the elements of the above-described various embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method comprising:
   determining, by a processor, whether an event sequence exists for an identifier;
   initiating, by the processor, the event sequence for the identifier, in response to the event sequence not previously existing,
   wherein the identifier is associated with a shipping event as an initial event for the identifier, and
   wherein the shipping event is associated with a current aggregation event;
   setting, by the processor, a state of the identifier to a reflecting error condition, in response to a decommissioning event existing earlier in the event sequence than the shipping event;
   storing, by the processor, the identifier in a database as ungrouped data elements formatted as a block of binary (BLOB);
   tuning, by the processor, the database to optimize database performance;
   obtaining, by the processor, the identifier from the database for the shipping event;
   setting, by the processor, the state of the identifier to a missing aggregation event condition, in response to the event sequence not previously existing and the identifier being for a container;
   setting, by the processor, the state of the identifier to a reflecting error condition, in response to a disaggregation event existing earlier in the event sequence than the current aggregation event, the identifier is for a container that is not reusable, and the identifier is a parent identifier in the disaggregation event; and
   setting, by the processor, the state of the identifier to the reflecting error condition, in response to an aggregation event not existing earlier in the event sequence than the current aggregation event, and the identifier is for the container that is not reusable.

2. The method of claim 1, further comprising setting, by the processor, the state of the identifier to the reflecting error condition, in response to at least one of:
   more than one commissioning event or no commissioning event existing earlier in the event sequence than the shipping event, and the identifier is for the item;
   more than one commissioning event or no commissioning event existing earlier in the event sequence than the shipping event, and the identifier is for the container that is not reusable; or
   an aggregation event not existing where the identifier is a parent identifier earlier in the event sequence than the current aggregation event but later than any receiving event, a disaggregation event not existing where the identifier is a parent identifier earlier in the event sequence than the current aggregation event but later than any receiving event, and the identifier is for a container that is reusable.

3. The method of claim 1, wherein the decommissioning event includes identifying at least one of an item that is sellable, a container associated with an item, or disaggregation hierarchies for an item.

4. The method of claim 1, further comprising receiving the decommissioning event issued in response to at least one of destruction of an unconsumed item, an expired item, a damaged item, a recalled item, an item being dispensed, an item being consumed, or an item being discarded.

5. The method of claim 2, further comprising:
   determining, by the processor, whether a decommissioning event exists in the event sequence for the item; and
   generating, by the processor, an error status for the item, in response to the determination that the decommissioning event exists in the event sequence for the item.

6. The method of claim 2, further comprising:
   determining, by the processor, whether a receiving event exists in the event sequence for the item;
   determining, by the processor, whether an associated shipping event exists for the receiving event; and
   generating, by the processor, an error status for the item, in response to the determination that there is not the associated shipping event for the receiving event.

7. The method of claim 2, further comprising:
   determining, by the processor, whether the shipping event exists in the event sequence for the item;
   determining, by the processor, whether a receiving event exists for the shipping event; and
   generating, by the processor, an error status for the item, in response to the determination that there is not an associated receiving event for the shipping event.

8. The method of claim 1, further comprising:
   determining, by the processor, whether the event sequence exists for the identifier; and
   initiating, by the processor, the event sequence for the identifier, in response to the event sequence not previously existing for the identifier.

9. The method of claim 1, wherein the shipping event includes at least one of a state or change of the state associated with the item.

10. The method of claim 1, further comprising:
    determining, by the processor, whether a plurality of decommissioning events exist in the event sequence for the item; and
    generating, by the processor, a suspect status for the item, in response to the determination that the plurality of decommissioning events exists in the event sequence for the item.

11. The method of claim 1, further comprising:
    identifying, by the processor, one or more contiguous chains of events within the event sequence;
    matching, by the processor, one or more pairs of events;
    forming, by the processor, one or more trees of links from the matched pairs of events; and identifying, by the processor, each tree as one of the contiguous chains of events.

12. The method of claim 1, further comprising adding, by the processor and in response to a condition reflecting error, a subset of the items associated with the identifier to be commissioned at least one of on a production line, as a shipment is being packed, or by a wholesaler.

13. The method of claim 1, further comprising creating, by the processor, at least one of a new link for related events or an unlinked event by utilizing a rules engine.

14. The method of claim 1, further comprising removing, by the processor and in response to the condition reflecting error, a subset of items associated with the identifier.

15. The method of claim 1, further comprising:
receiving, by the processor, a set of custom rules from an entity in a supply chain; and
assessing, by the processor, the shipping event by utilizing the set of custom rules.

16. The method of claim 1, further comprising:
reading, by the processor, a plurality of stored parameters from an entity in a supply chain;
creating, by the processor, a set of custom rules for the entity; and
assessing, by the processor, the shipping event by utilizing the set of custom rules.

17. The method of claim 1, further comprising reporting, by the processor and in accordance with a rule, a second commissioning event of an item as suspect, in response to identifying a first commissioning event of the item, and determining that the item has not been decommissioned subsequent to the first commissioning event.

18. The method of claim 1, further comprising:
determining, by the processor and in a recursive manner, additional identifiers from parent and child containment relationships;
associating, by the processor, the shipping event with the additional identifiers; and
setting, by the processor, a state of the identifier to a missing commissioning event condition, in response to the event sequence not previously existing and the identifier being for an item.

19. A method comprising:
determining, by a processor, whether an event sequence exists for an identifier;
initiating, by the processor, the event sequence for the identifier, in response to the event sequence not previously existing,
wherein the identifier is associated with a receiving event as an initial event for the identifier, and
wherein the receiving event is associated with a current aggregation event;
setting, by the processor, a state of the identifier to a reflecting error condition, in response to a decommissioning event existing earlier in the event sequence than the receiving event;
storing, by the processor, the identifier in a database as ungrouped data elements formatted as a block of binary (BLOB);
tuning, by the processor, the database to optimize database performance;
obtaining, by the processor, the identifier from the database for the receiving event;
setting, by the processor, the state of the identifier to a missing aggregation event condition, in response to the event sequence not previously existing and the identifier being for a container;
setting, by the processor, the state of the identifier to a reflecting error condition, in response to a disaggregation event existing earlier in the event sequence than the current aggregation event, the identifier is for a container that is not reusable, and the identifier is a parent identifier in the disaggregation event; and
setting, by the processor, the state of the identifier to the reflecting error condition, in response to an aggregation event not existing earlier in the event sequence than the current aggregation event, and the identifier is for the container that is not reusable.

* * * * *

UNITED STATES PATENT AND TRADEMARK OFFICE
CERTIFICATE OF CORRECTION

| | | |
|---|---|---|
| PATENT NO. | : 11,836,670 B2 | Page 1 of 1 |
| APPLICATION NO. | : 18/160884 | |
| DATED | : December 5, 2023 | |
| INVENTOR(S) | : David Bolene et al. | |

It is certified that error appears in the above-identified patent and that said Letters Patent is hereby corrected as shown below:

In the Claims

Claim 12, Column 37, Line 5, delete "a subset of the items" and insert --a subset of items--

Signed and Sealed this
Thirteenth Day of August, 2024

Katherine Kelly Vidal
*Director of the United States Patent and Trademark Office*